US007012061B1

(12) United States Patent
Reiss et al.

(10) Patent No.: US 7,012,061 B1
(45) Date of Patent: Mar. 14, 2006

(54) METHOD FOR INCREASING THE PERMEABILITY OF THE BLOOD BRAIN BARRIER

(75) Inventors: Carol Shoshkes Reiss, New York, NY (US); Takaishi Komatsu, Whitestone, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/807,826

(22) PCT Filed: Oct. 19, 1999

(86) PCT No.: PCT/US99/24442

§ 371 (c)(1),
(2), (4) Date: Aug. 22, 2001

(87) PCT Pub. No.: WO00/23102

PCT Pub. Date: Apr. 27, 2000

Related U.S. Application Data

(60) Provisional application No. 60/104,817, filed on Oct. 19, 1998.

(51) Int. Cl.
*A01N 37/18* (2006.01)

(52) U.S. Cl. ............................................. 514/2

(58) Field of Classification Search .................... 435/4; 514/2
See application file for complete search history.

(56) References Cited

U.S. PATENT DOCUMENTS

| 5,527,527 A | 6/1996 | Friden |
| 5,604,198 A | 2/1997 | Poduslo et al. |
| 5,648,101 A * | 7/1997 | Tawashi ..................... 424/718 |
| 5,670,477 A | 9/1997 | Poduslo et al. |

OTHER PUBLICATIONS

Minami et al. "Roles of Nitric Oxide and prostaglandins in the Increased Permeabillity of the Blood-Brain Barrier Caused by Lipopolysaccharide"., Environmental Toxicology and Pharmacology. Jan. 1998, vol. 5, No. 1, pp. 35-41.
Barna et al. "Activation of Type III Nitric Oxide Synthase in Astrocytes Following a Neurotropic Viral Infection", Virology, 1996, vol. 223, pp. 331-343.

* cited by examiner

*Primary Examiner*—Ardin H. Marschel
(74) *Attorney, Agent, or Firm*—Browdy and Neimark, PLLC

(57) ABSTRACT

The present invention relates to a method for regulating the permeability of the blood brain barrier by administering a NOS-3 inhibitor to reduce the increased permeability of the blood brain barrier caused by a pathological condition or by administering a NOS-3 activator or nitric oxide donor to increase the permeability of the blood brain barrier. By increasing the permeability of the blood barrier, a therapeutic or diagnostic compound can be delivered across this barrier into the central nervous system.

6 Claims, 18 Drawing Sheets

1- UNSTIMULATED 2.5 hr
2- UNSTIMULATED 2.5 hr
3- UNSTIMULATED 5 hr
4- UNSTIMULATED 5 hr
5- STIMULATED 2.5 hr
6- STIMULATED 2.5 hr
7- STIMULATED 5 hr
8- STIMULATED 5 hr
9- CONTROL

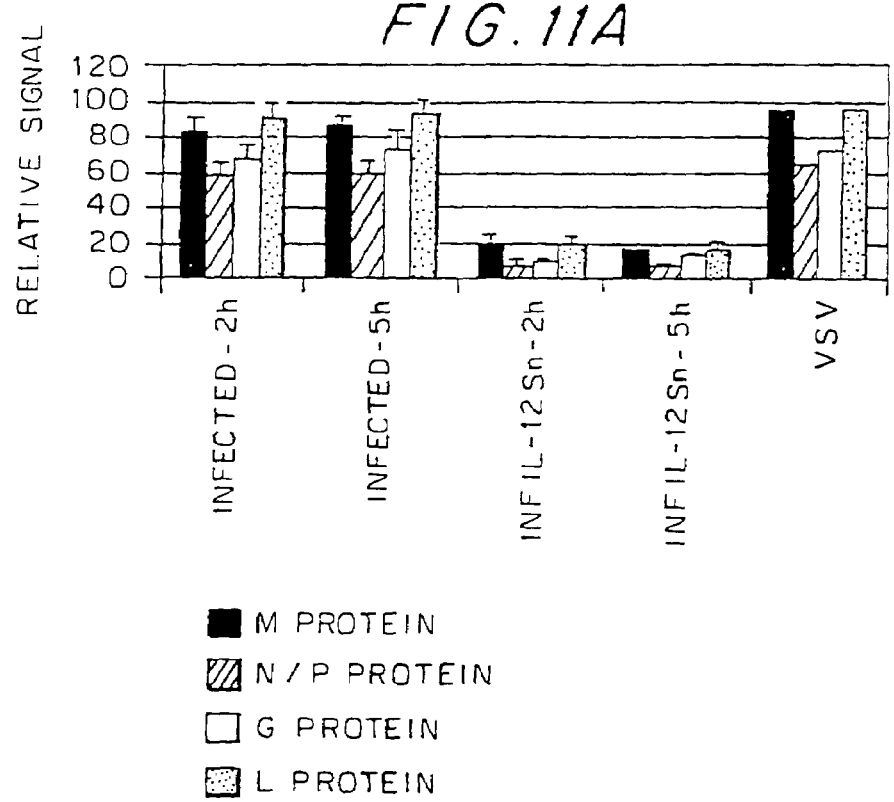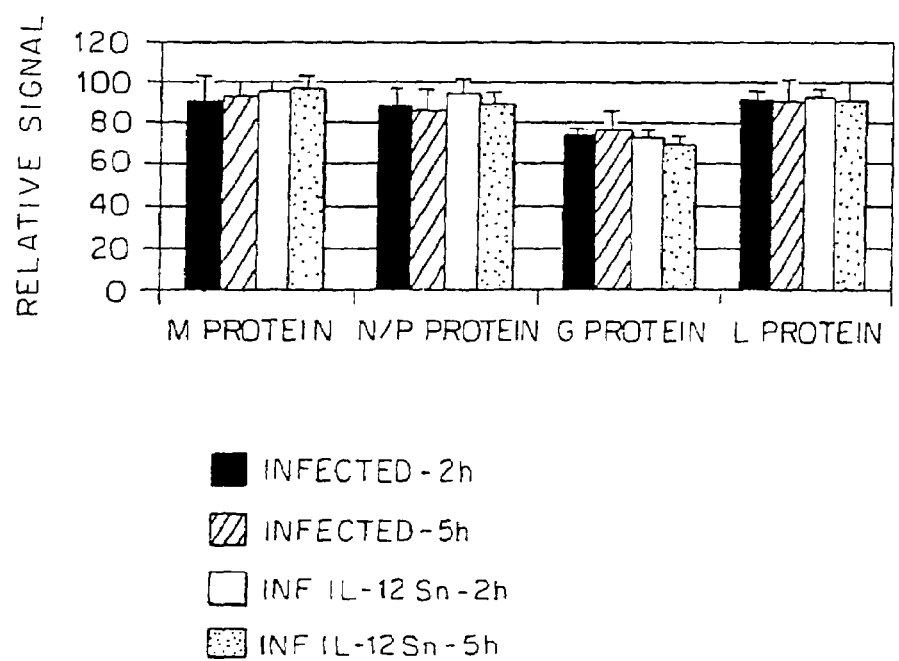

1 - UNSTIMULATED NB41A3
2 - UNSTIMULATED NB41A3
3 - UNSTIMULATED NB41A3
4 - STIMULATED NB41A3
5 - STIMULATED NB41A3
6 - STIMULATED NB41A3
7 - INFECTED CHO
8 - UNINFECTED CHO

WT + Med.

WT + IL-12

WT + VSV + Med.

WT + VSV + IL-12

N3-KO + Med.

N3-KO + IL-12

N3-KO + VSV + Med.

N3-KO + VSV + IL-12

WT + Med.

WT + IL-12

WT + VSV + Med.

WT + VSV + IL-12

N3-KO+Med.

N3-KO+IL-12

N3-KO+VSV+Med.

N3-KO+VSV+IL-12

METHOD FOR INCREASING THE PERMEABILITY OF THE BLOOD BRAIN BARRIER

REFERENCE TO RELATED APPLICATIONS

The present application is the national stage under 35 U.S.C. 371 of international application PCT/US99/24442, filed Oct. 19, 1999 which designated the United States, and which international application was published under PCT Article 21(2) in the English language w/c claims the benefit of 60/104,817 filed Oct. 19, 1998.

GOVERNMENT LICENSE RIGHTS

The experiments performed in this application were supported in part by the National Institute of Deafness and Communication Disorders, grant no. DC03536. The U.S. Government has a paid up license in this invention and the right in limited circumstances to require the patent owner to license others on reasonable terms as provided by the terms of the above grant.

BACKGROUND OF THE INVENTION

1. Field of the Invention

The present invention relates to a method for regulating the permeability or integrity of the blood brain barrier and a method for delivering a compound into the central nervous system by increasing the local permeability of brain microcapillary endothelial cells constituting the blood brain barrier.

2. Description of the Related Art

The central nervous system (CNS) has been traditionally considered an "immunologically privileged site" because of the inadequacy of immune response under normal conditions. The CNS is protected by the bones of the skull, meninges, the cerebrospinal fluid (CSF), and the blood brain barrier (BBB), a highly-selective vascular compartment which limits the flow of many biologically active molecules into the CNS. The CNS has no well defined lymphatic system or mechanism for antibody production and is isolated from the immune system in the absence of disease (Leibowitz et al, 1983). This "immunological privilege" may prevent the CNS from being damaged by excessive immune responses and may deter entry of pathogens in circulating cells. However, the CNS has been shown to be constantly under immune surveillance and is capable of terminating neurotropic infections by initiating effective antigen specific and non-specific response (Cserr et al, 1992; Fabry et al 1994; Lotan et al, 1994).

The BBB functions to regulate the constitution of the brain microenvironment essential for normal cerebral functions. The permeability of the BBB is determined by complex tight intercellular junctions between a highly-specialized group of microvascular endothelial cells located within the brain which restrict passage of macromolecules between the blood and the brain (Brightman et al, 1969). This highly-selective group of microvascular endothelial cells are characterized not only by extremely tight junctions between cells, but are also surrounded by the end-feet of astrocytes, and, more rarely, by perivascular pericytes. This capillary endothelial bed is distinct from capillaries in the periphery which are not fenestrated and have underlying smooth muscle cells.

During many types of clinical conditions, the integrity of the BBB in vivo becomes impaired and nitric oxide (NO) has been implicated in this process (Boje, 1996; Buster et al, 1995; Chi et al, 1994; Johnson et al, 1995; Mayhan, 1995; Thompson et al, 1992). Other mediators, such as PGE2 and small vasoactive complement products, have also been implicated. Proinflammatory cytokines, such as TNF-α and various interleukins, are also implicated in the pathogenesis of BBB breakdown (Goldblum et al, 1990; Tracey et al, 1990). Published investigations of BBB regulation have focused on endotoxic shock as a principal model and have indicated that downstream mediators of arachidonic acid, the cyclooxygenase (COX) lipoxygenase (LOX) pathways (prostaglandins and leukotrienes, respectively) are important effector molecules. These biochemical pathways are inhibited by non-steroidal anti-inflammatory drugs (NSAIDs). The laboratory of the present inventors has previously shown that vesicular stomatitus virus (VSV) infection may result in breakdown of the BBB (Bi et al, 1995a).

Perturbations of the BBB have been reported in a wide variety of CNS disorders and diseases, and the disruption of the integrity of the BBB selectivity can lead to drastic consequences to the individual. Brain vessels are normally impermeable to serum proteins due to the presence of tight junctions. Infection of brain endothelial cells may cause perturbations in BBB function, allowing toxic substances to cross into the normally inaccessible CNS. Modern understanding of brain pathophysiology has led to the provocative thought that many diseases of the CNS are associated with a failure of BBB integrity (Pardridge, 1986) Altered BBB permeability is commonly observed during ischemia, inflammation, trauma, neoplasia, hypertension, dementia and epilepsy (Buster et al, 1995; Chi et al, 1994; Mayhan, 1995; Prado et al, 1992; Shukla et al, 1995; Zhang et al, 1995). The extravasation of plasma proteins with BBB dysfunction may occur through a number of different transcellular or paracellular routes. This includes altered tight junctions, induction of fluid-phase or non-specific pinocytosis and transcytosis, formation of transendothelial channels or by disruption of the endothelial cell membrane (Durieu-Trautmann et al, 1993; Gross et al, 1991). From a therapeutic standpoint, the selectivity of the BBB serves to prevent the entry into the CNS of therapeutic drugs. For example, in the HIV infection of microglia, AZT and protease inhibitors are excluded by the BBB. Chemotherapeutic drugs are also excluded by the BBB and conventionally require administration intraventricularly, i.e., by catheter.

Viral infections of the CNS which disrupt the integrity of the BBB include viral encephalitis, such as from polio, measles, herpes, VSV, rabies, etc. Recently, data from many laboratories, using both RNA and DNA viruses in in vitro and in vivo experimental systems, have implicated a role for NO in the immune response. The data do not indicate a magic bullet for all systems but suggest that NO may inhibit an early stage in viral replication and thus prevent viral spread, promoting viral clearance and recovery of the host.

The earliest host responses to viral infections are non-specific and involve the induction of cytokines, among them interferons (IFNs) and tumor necrosis factor alpha (TNF-α). Gamma IFN (IFN-γ) and TNF-α have both been shown to be active in many cell types and induce cascades of downstream mediators (reviewed in Levy, 1997; O'Shea, 1997; Staeheli, 1990). Others have found that NO synthase type 2 (NOS-2, iNOS) is an IFN-γ-inducible protein in macrophages, requiring IRF-1 as a transcription factor (Ding et al, 1988; Kamijo et al, 1994). The laboratory of the present inventors has observed that the isoform expressed in neurons, NOS-1, and the isoform expressed in astrocytes and endothelial cells, NOS-3, are IFN—Y, TNF-α and interleukin-12 (IL-12) inducible. Thus, NOS falls into the category of IFN-inducible proteins activated during innate immune responses.

NO, which is the smallest, lightest molecule known to act as a biological messenger in mammals, was first identified as an endothelial cell relaxing factor (Furchgott et al, 1980; Palmer et al, 1987). There are three well-characterized isoforms of nitric oxide synthases (NOS). All three enzymes have binding domains for calmodulin, flavin monocludeotide, flavin adenine dinucleotide, NADPH and a heme-binding site near the N-terminus (Table 1)

TABLE 1

| Isoform | Other Name(s) | Cellular Expression | Regulation | Activity |
|---------|---------------|---------------------|------------|----------|
| NOS-1 | bNOS, ncNOS | neurons; dystrophin complex of striated muscle | $Ca^{2+}$ dependent soluble; constituitively expressed but also inducible with cytokines (IFN-γ, IL-12 and TNF-α) | short bursts of small quantity NO |
| NOS-2 | iNOS | macrophages; EBV-transformed B cells; HeLa cells | $Ca^{2+}$ independent; soluble; inducible with lipopolysaccharide, IFN-γ and TNF-α | long bursts of large quantity NO |
| NOS-3 | eNOS, ecNOS | endothelial cells; astrocytes, ependymal cells | $Ca^{2+}$ dependent; membrane bound; constituitively expressed but also inducible with cytokines; estrogen response element | short bursts of small quantity NO |

NO has an unpaired electron; thus, its effects are mediated through other molecules that accept or share this odd electron (Butler et al, 1995; Gaston et al, 1994). Target molecules include oxygen, other free radicals, thiol groups and metals. However, NO is relatively less reactive than other oxygen radicals, such as superoxide anion ($O_2^-$) and hydroxyl radical ($OH^-$), making it a more stable carrier of unpaired electrons.

No has a short half-life, in the range of a few seconds or less, and reacts readily with reduced cysteine moieties, yielding S-nitrosothiols that are somewhat stable with a half-life of minutes to hours. The amino acid L-arginine, a substrate for NO synthesis, contains two guanidine nitrogens that accept five electrons in an oxidation-reduction pathway, which results in the formation of L-citrulline and NO (Yun et al, 1996) (FIG. 1).

No is produced by the enzymatic modification of L-arginine to L-citrulline and requires many cofactors, including tetrahydrobiopterine, calmodulin, NADPH and $O_2$. NO rapidly reacts with proteins or with $H_2O_2$ to form $ONOO^-$, peroxynitrite, which is highly toxic (FIG. 1). NO also readily binds heme proteins, including Hb and its own enzyme.

The combination of NO with $O_2^-$ forms peroxynitrite ($ONOO^-$), which has the capacity to injure target cells (Beckman et al, 1996). When NO interacts with prosthetic iron groups or thiol groups on proteins, it can form complexes that activate or inactivate target enzymes. Although the action of NO is mostly local, NO has the capacity to move rapidly to distant target molecules. Unlike many messenger molecules and secretory molecules that use membrane receptors or specific supporters, NO is so lipophilic that it readily diffuses across membranes. Thus, NO can rapidly move from cell to cell, has a short range and duration of action, but exhibits high biological activity.

The neuronal NOS isoform (ncNOS, bNOS, NOS-1) is constitutively expressed and postranscriptionally regulated. Activity is dependent on calcium and calmodulin. It exists as a cytosolic homodimer under native conditions (Marletta, 1994). Enzyme levels are cytokine inducible (Barna et al, 1996; Komatsu et al, 1996). The macrophage form (NOS-2, iNOS) is rapidly induced by lipopolysaccharide (LPS), TNF-α, IL-12 and IFN-γ treatment, and is independent of calcium. NOS-2 is a cytosolic dimer under native conditions (Marletta, 1994). In the CNS, it is expressed in some astrocytes, microglia and inflammatory monocytes (Amin et al, 1995a; Galea et al, 1994; Merill et al, 1993; Zielasek et al, 1992). The endothelial form (NOS-3 ecNOS) is constitutively expressed by posttranslationally regulated and PI linked membrane associated. Like NOS-1, it is dependent on calcium and calmodulin. It is expressed in a subset of neurons and endothelial cells (Dawson et al, 1994); the laboratory of the present inventors has shown that astrocytes in the CNS synthesize NOS-3 (Barna et al, 1996) and ependymal cells (unpublished results).

Immunologically, NOS activity, NOS-immunoreactive proteins and mRNA have been found in autoimmune diseases, such as multiple sclerosis, associated with demyelinating lesions (DeGroot et al, 1997) and arthritic joints (Shiraishi et al, 1997) and are thought to contribute to disease pathogenesis. NOS is frequently observed to be induced during the immune response (Barna et al, 1996). In contrast, in many intracellular bacterial and parasitic infectious diseases, NOS activity has been observed to be essential in eliminating pathogens, such as *Plasmodium falciparum* (Anstey et al, 1996).

NO has been demonstrated to be a key component in host defense against a variety of pathogens, including protozoan parasites, fungi, bacteria and viruses (Harris et al, 1995; Karupiah et al, 1993; Lee et al, 1994; Seguin et al, 1994; Stenger et al, 1994; and reviewed by Reiss et al, 1998). It has inhibitory effects on ectromelia, vaccinia and herpes simplex type-1 viruses in macrophages (Karupiah et al, 1993) and the murine Friend leukemia virus (Akarid et al, 1995). It also has an inhibitory effect on HIV replication (Mannick et al, 1996).

A number of recent publications relate to the relationship between NO or NOS and the disruption or change in permeability of the BBB (Janigro et al, 1994; Dirnagle, 1996; Mayhan et al, 1996; Mayhan, 1996; Hurst et al, 1996; Chi et al, 1994; Boje 1995 and 1996; Shukla et al, 1996; Nakano et al, 1996). Boje (1995) disclosed that LPS injected into ventricles induced meningeal NO production and BBB permeability. However, the administration of amino guanidine, an inhibitor of NOS, blocked meningeal NO production and attenuated the increased permeability of the BBB observed in a rat model of meningitis. Shukla et al (1996) concluded from their results that NO itself causes an increase in the permeability of the BBB. In a study to determine whether NO mediates the selective increase in brain tumor microvessel permeability after intracarotid infusion of the vasodilator bradykinin in the RG2 rat glioma model, Nakano et al (1996) reported that transport of a tracer into brain tumors was selectively increased by the intracarotid infusion of bradykinin. Transport into normal brain was not increased. This was significantly inhibited by a NOS inhibitor, NG-nitro-L-arginine methylester. Nakano et al indicate that the selective permeability increase in brain tumor microvessels after bradykinin infusion is mediated by NO and speculate that the absence of high levels of NOS in normal brain may account for the attenuated permeability response to bradykinin in normal brain microvessels. However, the results reported in these publications on altered BBB permeability were all obtained in disease models in which the effector molecules for BBB permeability were present systemically in the animal model. There is, furthermore, no disclosure or suggestion of delivering a therapeutic compound into the CNS through increased BBB permeability by activating NOS-3.

Currently, the art has focused on regulation of NOS-3 in the periphery to control blood pressure or to relax coronary arteries during angina, and more recently, to enhance male sexual performance through sustaining erections. BBB effects are inadvertently related to gram-negative bacterial infections resulting in "shock".

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention is based on the discovery that the constitutive endothelial isoform of nitric oxide synthase (NOS-3) is central to the integrity of the blood brain barrier and provides a method for regulating the permeability of this barrier. One aspect of the method according to the present invention reduces the increased permeability of the blood brain barrier as a result of a pathological condition by locally administering a NOS-3 inhibitor, and another aspect increases the permeability of the blood brain barrier by locally administering a NOS-3 activator or nitric oxide donor, thereby avoiding the problems associated with the systemic administration of NOS-3 inhibitors or activators.

A further aspect of the method according to the present invention is to provide for systemic administration of a NOS-3 inhibitor which is associated with a targeting molecule specific for cells forming the blood brain barrier. The association of the NOS-3 inhibitor with the targeting molecule delivers the NOS-3 inhibitor directly to the blood brain barrier and moreover avoids the problems associated with systemic administration of NOS-3 inhibitors and their prolonged presence in the circulation.

Further provided by the present invention is a method for delivering a neurologically active therapeutic compound or diagnostic compound into the central nervous system by the contemporaneous local administration of a NOS-3 activator or a nitric oxide donor or by the systemic administration where the therapeutic or diagnostic compound is in association with both a targeting molecule and a NOS-3 activator or nitric oxide donor.

BRIEF DESCRIPTION OF THE DRAWINGS

FIGS. 11A and 11B show the dual staining of the gels. The gels from FIGS. 8 and 9 were simultaneously stained for VSV (FIG. 11A) and nitrosine (FIG. 11B).

FIG. 21A shows WT mice and FIG. 21B shows N3-KO mice. All of the groups, except WT+VSV, showed no statistical difference in comparison to each other. All of these groups show statistical difference from the WT+VSV group.

DETAILED DESCRIPTION OF THE INVENTION

Figure 1:
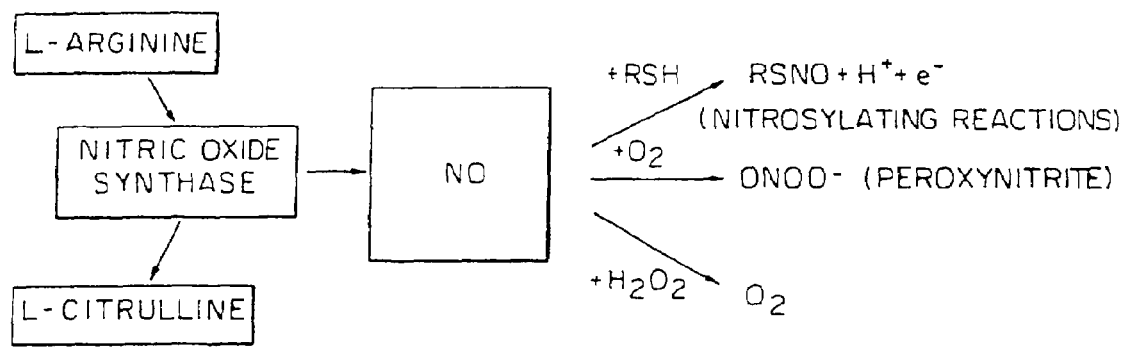
FIG. 1 shows the enzymatic formation of NO and its reaction with proteins and other compounds.

The present inventors have conducted experiments that provided a novel insight into some of the important features of the BBB which have otherwise been overlooked by investigators in the field. The present invention is based on the discovery of the present inventors, using the viral encephalitis model, that a specific enzyme system, the constitutive endothelial cell isoform NOS-3, is central to the integrity of the BBB.

As previously reported by the laboratory of the present inventors, it was found that approximately half of the infected normal mice (BALB/c or B6) succumb to infection, accompanied by hindlimb paralysis and disruption of the BBB, as measured by the failure to exclude Evans blue dye injected intravenously (Bi et al, 1995a; Christian et al, 1996; Komatsu et al, 1997). When infection is controlled by providing exogenous IL-12, which limits early viral replication and prevents caudal spread of virus, there is no disruption of the BBB, and mice are relatively protected from lethal infection. IL-12 can be administered up to at least one day after infection and have the beneficial effect (unpublished results).

The laboratory of the present inventors has found ultrastructural changes in the BBB associated with infection. For example, capillary diameter increases substantially and the tight junctions of brain microvascular capillary endothelial cells increase in distance. There were also changes in the ependymal cells lining the fourth ventricle, which showed increased distances in the tight junctions. The present inventors then conducted survival, CNS viral titers, Evans blue dye exclusion and immunohistochemical studies in three knock-out mouse strains (IFN-$\gamma$ deficient, NOS-1 deficient and NOS-3 deficient) and their appropriate control strains of mice. Based on the substantially increased viral titers and the immunohistochemical analyses, NOS-3 deficient mice were expected to succumb to acute infection. However, these mice surprisingly survived, were similar to wild-type control mice in their mortality and were not found to have uptake of the blue dye. In contrast, NOS-1 deficient mice readily died from the infection and had earlier and more profound breakdown of the BBB.

From these results, the present inventors concluded that NOS-3 in endothelial cells (and perhaps also the astrocytes which have end-feet on the endothelial cells (Barna et al, 1996) and the ependymal cells which serve as a barrier to the ventricles and overlie capillaries) causes relaxation of the endothelial cell wall of the brain microvascular capillaries and ependymal cells, which then results in the flow of excluded substances and fluid into the brain parenchyma. This is consistent with breakdown of the BBB.

The method for regulating the permeability of the BBB, according to the present invention, involves the administration of a NOS-3 regulating agent. To increase the permeability of the BBB, the NOS-3 regulating agent is a NOS-3 activator or NO donor. Conversely, to reduce an increased permeability of the BBB caused by a pathological condition, the NOS-3 regulating agent is a NOS-3 inhibitor/antagonist. Such a pathological condition is any abnormal condition which causes BBB permeability to increase as a result of said condition, examples of which include, but are not limited to, stroke (ischemia), peripheral gram negative bacterial infections (via cytokine storm), bacterial toxins (e.g., LPS, pertussis toxin) and CNS infections (i.e., viral infections, which include lymphocytic choriomeningitis, VSV, bacterial infections; fungal infections; parasitic infections, such as malaria). Non-limiting examples of NOS-3 inhibitors/antagonists include analogs of L-arginine, such as $N^G$-Monomethyl-L-Arginine (L-NMMA), L-N-Methyl Arginine (L-NMA), $N^G$-Nitro-L-Arginine Methyl Ester (L-NAME), 7-nitroindazole (7-NI). It is preferred, although not necessary, that the NOS-3 inhibitor/antagonist be selective for the NOS-3 isoform. In other words, the NOS-3 inhibitor/antagonist preferably has a negligible or low $K_i$ with the NOS-1 and NOS-2 isoforms relative to its $K_i$ with the NOS-3 isoform. Using such a selective inhibitor of NOS-3 would avoid or limit any unintended inhibition of NOS-1 and NOS-2 activities.

Furthermore, because parenteral or oral administration may lead to unintended systemic side-effects, the NOS-3 regulating agent is administered either locally, such as injection into the cervical artery, close to the BBB so that there is little or no exposure outside of the local area of administration to the NOS-3 regulating agent, or systemically in a manner which targets the NOS-3 regulating agent specifically to cells forming the BBB, such as the microvascular endothelial cells of the brain.

When the NOS-3 regulating agent is a NOS-3 activator or NO donor for increasing the permeability of the BBB, a further embodiment of the method of the present invention is to contemporaneously deliver a neurologically active therapeutic compound or a diagnostic compound into the CNS through the permeable BBB. Preferably, the increased permeability of the BBB is temporary, and more preferably, the increased permeability of the BBB is of a short duration, just sufficient for delivering the therapeutic or diagnostic compound across the BBB. In this embodiment where administration of a NOS-3 activator or NO donor is local, the NOS-3 activator or NO donor is preferably co-administered together with the therapeutic or diagnostic agent sought to be delivered to the CNS. Examples of pathological conditions in which it would be desirable to deliver therapeutic or diagnostic compounds to the CNS include infections (i.e., highly-active anti-retroviral therapy for HIV or antibiotics for bacterial infection), primary CNS tumors or secondary metastases (i.e., chemotherapeutic drugs to treat primary gliomas, astrocytomas and meningiomas, and secondary lymphomas, and breast, liver, pancreatic and colon metastatic cells), Alzheimer's Disease, etc.

Currently, there are many markers available for identifying primary CNS tumors, as well as secondary metastases from tumors outside the CNS. While these markers are commonly available to hospitals and many are routinely used in diagnosis elsewhere in the body, such as for secondary metastases from cancer cells originating from the breast, liver, pancreas, colon, etc., there is no non-invasive method for readily administering these markers for diagnostic imaging of the brain. Accordingly, the method of the present invention provides a means of delivering therapeutic as well as diagnostic compounds, which can be imaged, across the BBB.

Non-limiting examples of NOS-3 activators and NO donors include nitroglycerin, histamine, L-glutamic acid, calcimycin, sodium nitroprusside (SNP), S-nitroso-L-acetylpenicillamine (SNAP), 3-morpholino-sydononimine (SIN-1), cytokines which trigger $Ca^{++}$ flux and also induce neosynthesis of NOS-3 (i.e., IFN-γ, TNF-α, IL-12), etc. There is a wealth of NOS inhibitors/antagonists, activators and NO donors known to those of skill in the art, many of which are available commercially from suppliers, such as Calbiochem/Oncogene Research Products (San Diego, Calif. and Cambridge, Mass.), Sigma-Aldrich Co. (St. Louis, Mo.), Cayman Chemical (Ann Arbor, Mich.), Oxford Biomedical Research, Inc. (Oxford, Mich.), Alexis Corp. (San Diego, Calif.), etc.

In the embodiment in which the NOS-3 regulating agent may be administered systemically to regulate the permeability of the BBB, the NOS-3 regulating agent is associated with a targeting molecule which is specific for the cells forming the BBB. Such an association may be by conjugation or by the formation of a complex, etc., where the association is stable to transport from the site of administration to the targeted cells of the BBB.

By "targeting molecule" which is specific for the cells forming the BBB, it is intended that the "targeting molecule" be any molecule which specifically recognizes or is recognized by a cell surface marker on cells forming the BBB. Generally, this recognition involves binding. The "targeting molecule" can be, for example, a ligand for a cell surface receptor or a molecule having the antigen-binding portion of an antibody which recognizes and binds to an epitope of a cell surface marker.

It should be understood that, when the term "antibody" or "antibodies" is used herein, this is intended to include intact antibodies, such as polyclonal antibodies or monoclonal antibodies (mAbs), as well as proteolytic fragments thereof such as the Fab or F(ab')$_2$ fragments. Furthermore, the DNA encoding the variable region of the antibody can be inserted into other antibodies to produce chimeric antibodies (see, for example, U.S. Pat. No. 4,816,567). Single-chain antibodies can also be produced and used. Single-chain antibodies can be single-chain composite polypeptides having antigen-binding capabilities and comprising a pair of amino acid sequences homologous or analogous to the variable regions of an immunoglobulin light and heavy chain (linked $V_H$–$V_L$ or single-chain $F_V$). Both $V_H$ and $V_L$ may copy natural monoclonal antibody sequences or one or both of the chains may comprise a CDR-FR construct of the type described in U.S. Pat. No. 5,091,513. The separate polypeptides analogous to the variable regions of the light and heavy chains are held together by a polypeptide linker. Methods of production of such single-chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815.

A "molecule which includes the antigen-binding portion of an antibody" is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, and chimeric humanized or single-chain antibodies incorporating such reactive fraction, as well as any other type of molecule in which such antibody reactive fraction has been physically inserted or molecules developed to deliver therapeutic moieties by means of a portion of the molecule containing such a reactive fraction. Such molecules may be provided by any known technique, including, but not limited to, enzymatic cleavage, peptide synthesis or recombinant techniques, such as phage display libraries.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules, such as amino acids or sugar side chains and have specific three-dimensional structural characteristics, as well as specific charge characteristics.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be obtained by methods known to those skilled in the art. See, for example Kohler et al (1975); U.S. Pat. No. 4,376,110; Ausubel et al (1987–94); Harlow et al (1988); and Coligan et al (1993). Such antibodies may be of any immunoglobulin class including IgG, IgM, IgE, IgA, IgD and any subclass thereof. The hybridoma producing the mAbs may be cultivated in vitro or in vivo. High titers of mAbs can be obtained in in vivo production where cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric (humanized) mAbs are used. Chimeric antibodies and methods for their production are known in the art (Cabilly et al, 1984; Morrison et al, 1984; European Patent Application 125023; Neuberger et al, 1985; European Patent Application 171496; European Patent Application 173494; PCT Application WO 8601533; European Patent Application 184187; European Patent Application 173494; Sahagan et al, 1986; WO 9702671; Liu et al, 1987; Sun et al, 1987; Better et al, 1988; and Harlow et al, 1998).

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880.

The anti-Id antibody may also be used as an "immunogen" to induce an immune response in yet another animal, producing a so-called anti-anti-Id antibody. The anti-anti-Id may bear structural similarity to the original mAb which induced the anti-Id. Thus, by using antibodies to the idiotypic determinants of a mAb, it is possible to identify clones expressing antibodies of identical specificity.

As mentioned above, the term "antibody" is also meant to include both intact molecules, as well as fragments thereof, such as, for example, Fab and F(ab')$_2$, which are capable of binding antigen. Fab and F(ab')$_2$ fragments are preferably used as targeting molecules because they lack the Fc fragment of intact antibody, clear more rapidly from the circulation and may have less non-specific tissue binding than an intact antibody (Wahl et al, 1983).

While there are many techniques known in the art to identify cell surface markers (and ligands that are bound thereto), the well-known technique of making antibodies by in vitro phage display can be advantageously used to bypass hybridoma technology and immunization. Such an in vitro technique uses the V gene repertoires harvested from populations of lymphocytes or assembled in vitro for cloning and display of associated heavy and light chain variable domains on the surface of a filamentous bacteriophage (Winter et al, 1994). From a phage library containing the V gene repertoire, phage which bind to an antigen from the surface of cells forming the BBB are selected. Nucleic acid isolated from the selected phage which bind specifically to the surface of the cells forming the BBB are then introduced into host cells to express soluble antibody fragments. The affinity of the soluble antibody fragments for the cell surface antigen can be improved by mutagenesis of the DNA coding for the soluble antibody fragments in the host cells.

Many laboratories have used in vitro antibody phage display libraries to screen or "pan" for phage displayed antibodies against specific antigens, and a representative though certainly not exhaustive, list of citations include Sawyer et al (1977); Waters et al (1997); Figini et al (1998); Chowdhury et al (1997); Pfistermueller et al (1996); Kakinuma et al (1997); Iba et al (1997); Pereira et al (1997a and 1997b); Siegel et al (1997); and Osbourne et al (1996). Some laboratories have established whole cell based systems for a screening procedure for the detection and isolation of cell surface antigens and procedures for optimizing the capture of cell surface specific antibodies using antibody phage display (Watters et al, 1997; Chowdhury et al, 1997; Pereira et al, 1997a and 1997b; Siegel et al, 1997). For instance, Siegel et al (1997) optimized the capture of cell surface specific human antibodies using phage display and minimized the binding of irrelevant phage displayed antibodies using a simultaneous positive and negative selection strategy.

A specific example of a method for panning antibodies against cell surface antigens using in vitro antibody phage display is a method derived from Palmer et al (1997), where a single pot of human Fv semi-synthetic filamentous phage display library is to be constructed in the pHEN1 vector according to the procedure of Nissim et al (1994). The library will be rescued with VC3M13 helper phage (Stratagene, La Jolla, Calif.), and the phage will be purified using polyethylene glycol. For each round of selection for phage which bind to brain microcapillary endothelial cells (BMEC), approximately $10^{13}$ transducing units of phage in PBS with 5% milk powder (for non-specific blocking) will be added to target BMEC and incubated overnight at 4° C. Cells will then be washed with PBS, 1% albumin, to remove unbound phage. Bound phage will be eluted from BMEC by adding 300/1 of 76 mM citric acid in PGS (pH 2.5), and the fluid neutralized with 400 µl 1M Tris-HCl, pH 7.4. The phage will be subsequently expanded overnight in E. coli TG1 cells.

Phage particles will be enriched for specific high-affinity antigen binding phage through a further five rounds of binding to BMEC, and screening for binding to a panel of cell types, such as dermal microcapillaries, foreskin microcapillaries, umbilical vein endothelial cells, aorta and standard human cell lines derived from cornea, keratinocytes, kidney, etc., to determine cell and tissue specificity. Only those phage which exclusively bind BMEC will be used for further experiments. The plasmid carried by the selected phage which encode the Fv segment(s) will be isolated, characterized and cloned for expression in bacterial host cells to produce a soluble Fv segment(s) that can be purified and used for derivatization with cross-linkers for drug delivery.

The soluble antibody fragments produced according to the above procedure can be used as targeting molecules for delivering a NOS-3 regulating agent to the BBB upon systemic administration to a subject. The association of a NOS-3 regulating agent with an antibody as a targeting molecule is preferably by conjugation.

In addition, physiological ligands of cell surface receptors specific for brain microvascular endothelial cells constituting the BBB can be identified without undue experiment according to well-known screening techniques, etc., once a cell surface receptor specific to brain microvascular endothelial cells has been characterized, i.e., using antibodies from a phage display library that binds specifically to cell surface antigens as discussed above.

There are many approaches for the chemical cross-linking or "conjugation" of proteins. Significant advancement in the application of these cross-linking agents has led to the synthesis of cleavable bifunctional compounds. There are over 300 cross-linkers now available, and it is clear to those of skill in the art that multiple approaches can be used to chemically cross-link therapeutic agents or other compounds, such as NOS-3 regulating agent, to proteins or peptides, such as antibodies or antibody fragments. Moreover, based on the bifunctionality of these cross-linking agents, they can also be used to conjugate a therapeutic agent, a ligand or an antibody, and a NOS-3 regulating agent to each other in any combination. In the method of the present invention, the conjugation or cross-linking of a therapeutic agent to one of the above-mentioned protein or peptide molecules can be accomplished in a manner so that the ability of the protein or peptide to bind to its cell surface marker is not significantly altered, nor is the bioactivity of the therapeutic agent or NOS-3 regulating agent significantly affected by the cross-linking procedure.

Numerous considerations, such as reactivity, specificity, spacer arm length, membrane permeability, cleavability and solubility characteristics need to be evaluated when choosing an appropriate cross-linker. A recent review of the "Chemistry of Protein Conjugation and Cross-Linking" can be found by Shan S. Wong, CRC Press, Ann Arbor (1991). The most important question, perhaps, is what functional groups are available for coupling. These functional groups must not be involved in the binding to the cell surface marker or the inactivation of the therapeutic agent. For example, if only lysines or the N-terminus are available, a logical choice would be NHS-ester homobifunctional cross-linkers. If one molecule has lysines and the other sulfhydryls, a maleimide NHS-ester cross-linker would be an appropriate choice. If only lysines are available on both molecules, modification to introduce sulfhydryls via the lysines on one molecule would allow for sequential coupling. If both molecules have free sulfhydryls, a homobifunctional sulfhydryl reactive cross-linker would be appropriate. If carboxyls and amines are available, carbodiimide works well. Furthermore, if there are no readily reactive groups, a photoactivatible cross-linker can be used. If lysines are important for the functionality of the molecule, then a cross-linker that will couple through sulfhydryls, carboxyls or non-specifically can be used.

To preserve the binding capacity or the bioactivity of one of the molecules to be conjugated, it may be necessary to choose an appropriate spacer arm length between a cross-linker and the conjugated molecule. Similarly, if solubility is a problem, and organic solvents are detrimental to the therapeutic agent or conjugation partner(s), then there are many commercially available water-soluble cross-linkers, such as the sulfonated NHS-ester homo- and heterobifunctional cross-linkers.

Conjugation or coupling reagents have at least two reactive groups and can be either homobifunctional with two identical reactive groups or heterobifunctional with two more different reactive groups. Trifunctional groups also exist and can contain three functional groups. Most homobifunctional cross-linkers react with primary amines commonly found on proteins. Other homobifunctional cross-linkers couple through primary sulfhydryls. Homobifunctional cross-linkers can be used in a one-step reaction procedure in which the compounds to be coupled are mixed and the cross-linker is added to the solution. The resulting cross-linking method may result in self-conjugation, intermolecular cross-linking, and/or polymerization. The following are examples of suggested cross-linking approaches and are not meant to be inclusive.

Imido esters are the most specific acylating reagents for reaction with the amine groups whereby in mild alkaline pH, imido esters react only with primary amines to form imidoamides. The product carries a positive charge at physiological pH, as does the primary amine it replaces and, therefore, does not affect the overall charge of the protein.

Homobifunctional N-hydroxysuccinimidyl ester conjugation is also a useful cross-link approach to cross-link amine-containing proteins. Homobifunctional sulfhydryl reactive cross-linkers include bismaleimidhexane (BMH), 1,5-difluoro-2,4-dinitrobenzene (DFDNB) and 1,4-di-(3',2'-pyridyldithio) propionamido butane (DPDPB).

Many heterobifunctional cross-linkers are commercially available with the majority containing an amine-reactive functional group on one end and a sulfhydryl-reactive group on the other end. Multiple heterobifunctional haloacetyl cross-linkers are available, as are pyridyl disulfide cross-liners. In addition, heterobifunctional cross-linking reagents which react with carboxylic groups involve the carbodiimides as a classic example for coupling carboxyls to amines resulting in an amide bond.

Another embodiment according to the present invention is to further associate a neurologically active therapeutic compound or diagnostic compound with a targeting molecule and a NOS-3 activator or NO donor for targeted delivery into the CNS. The association is preferably by conjugation or by formation of a complex. In this embodiment, a pharmaceutical composition containing the active ingredients can be advantageously administered systemically, as well as locally. The presence of the targeting molecule in association with the NOS-3 activator or NO donor and the therapeutic or diagnostic compound targets its delivery to the BBB and thereby beneficially limits the systemic exposure of the subject to the NOS-3 regulating agent, as well as to the therapeutic or diagnostic compound. Thus, this pharmaceutical composition can be administered by any means that achieves its intended purpose and is not limited to local administration in the vicinity of the BBB. For example, administration may be by various parenteral routes, such as subcutaneous, intravenous, intradermal, intramuscular, intraperitoneal, intranasal, transdermal or buccal routes. Alternatively, or concurrently, administration may be by the oral route. Parenteral administration can be by bolus injection or by gradual perfusion over time.

Preparations for parenteral, as well as local administration, include sterile aqueous or non-aqueous solutions, suspensions and emulsions, which may contain auxiliary agents or excipients which are known in the art and which may facilitate processing of the active compounds into preparations which can be used pharmaceutically. Pharmaceutical compositions, such as tablets and capsules can also be prepared according to routine methods.

Suitable formulations for administration include aqueous solutions of the active compounds in water-soluble form, for example, water-soluble salts. In addition, suspension of the active compounds as appropriate oily injection suspensions may be administered. Suitable lipophilic solvents or vehicles include fatty oils, for example, sesame oil, or synthetic fatty esters, for example, ethyl oleate or triglycerides. Aqueous injection suspensions that may contain substances which increase the viscosity of the suspension include, for example, sodium carboxymethyl cellulose, sorbitol and/or dextran. Optionally, the suspension may also contain stabilizers.

Having now generally described the invention, the same will be more readily understood through reference to the following example, which is provided by way of illustration and is not intended to be limiting of the present invention.

EXAMPLE

Vesicular stomatitis virus (VSV), a member of the Rhabdovirus family, is an enveloped, single-stranded, negative-sense RNA virus (Wagner, 1987). VSV encodes a single variable glycoprotein, a conserved matrix protein, a nucleoprotein, a large protein and phosphoproteins in overlapping reading frame (Wagner, 1987).

The natural host of VSV is the cow, and it is transmitted by an arthropod vector, commonly the sandfly. In cows, the infection is mild and causes the characteristic vesicle lesions in the oral cavity. There are two principal serotypes: Indiana and New Jersey (Clewley et al, 1977; Reichmann et al, 1978). Studies using VSV as a model system include viral entry (Fuller et al, 1984), membrane fusion (Bundo-Morita et al, 1988), targeting of proteins within cells (Lyles et al, 1988), viral assembly (Moyer et al, 1991), viral inhibition by interferons (Stewart, 1979), defective interfering viral particles (Browning et al, 1991; Huang et al, 1970), endogenous antigen presentation by MHC class II molecules (Reiss, 1993), viral immunity (Forger et al, 1991; Zinkernagel, 1993) and many others.

It has also been shown that intranasal instillation of VSV could lead to lethal infection of the CNS (Sabin et al, 1937), which has led to the use of VSV as a model for studies of neurotropic viral infections (Andersson et al, 1993; Bi et al 1995a; Cave et al, 1984; Forger et al, 1991; Huneycutt et al, 1993; Huneycutt et al, 1994; Lundh et al, 1987; Mohammed et al, 1990; Plakhov et al, 1995).

When administered intranasally to mice, VSV infects olfactory receptor neurons (Plakhov et al, 1995), is transmitted to neurons within the olfactory bulb, and then to more caudal regions of the CNS (Forger et al, 1991; Huneycutt et al, 1994; Lundh et al, 1987). Surviving mice completely clear the virus from the CNS by day 12 post infection (Forger et al, 1991). The laboratory of the present inventors has previously shown that VSV infection activates both innate immunity and acquired immunity (Bi et al, 1995a) and that recovery from infection requires T cell immunocompetence (Huneycutt et al, 1993). However, the mechanism(s) of host defense and recovery during VSV infection of the CNS remain unclear, and the experiments in this example were conducted to elucidate the role of NO and NOS isoforms in the CNS.

Materials and Methods

Viruses

VSV Indian serotype, San Juan strain, was propagated in Chinese Hamster Ovary (CHO) cells and twice purified using a sucrose gradient. Viral titers were determined on monolayers of CHO cells as previously described by Huneycutt et al (1993).

Herpes Simplex virus-1 was kindly provided by Dr. Priscilla A. Schaffer (Dana-Farber Cancer Institute). Influenza virus A/WSN/33 was provided by Dr. Peter Palese (Mount Sinai School of Medicine). Sindbis AR339 virus was the gift of Dr. Beth Levine (Columbia University).

Experimental Infection of Mice

Specific pathogen-free BALB/c AnTac mice (Taconic Farms, Inc., Germantown, N.Y.), C57BL/6 B6) WT mice, B6 IFN-γ KO mice (Jackson Laboratory, Bar Harbor, Me.), NOS-1 KO mice (breeding pairs provided by Dr. Fishman and Dr. Huang, MGH) and NOS-3 KO mice (MGH) were used throughout the experiment.

The mice were lightly anesthetized for one minute in a closed container containing Halothane™ (Halocarbon Lab, North Augusta, S.C.), followed by intranasal infection with $2\times10^5$ plaque-forming unit of VSV in a total volume of 0.01 mL administered equally through each nostril, as previously described by Bi et al (1995a). Ten mice in each treatment group were reserved for evaluation of morbidity (weight changes) and mortality (Plakhov et al, 1995). At each time point, at least 8 mice per treatment group were given a lethal dose of ketamine-xylazine. Five brains from each group were homogenized and frozen for later determination of viral titers, as previously described (Bi et al, 1995a; Forger et al, 1991). The lower limit of detection of the assay is 100 PFU/mL homogenate. The other three mice in each group were perfused transcardially with 20 to 30 mL of normal saline, and the whole brains were removed and quick-frozen in isopentene kept on dry ice before being stored at −70° C. until sectioning, as previously described (Bi et al, 1995a).

Protocol of In Vivo Treatment of IL-12

Murine rIL-12 was generously provided by Genetics Institute (Cambridge, Mass.). On the day of infection, groups of mice were injected i.p. daily with medium alone or 200 ng of IL-12/mouse; this was continued daily from 0 to 7 days post infection.

Immunohistochemical Reagents

TABLE 2

Primary Antibodies Used for Immunohistochemistry

| Antigen | Reagent | Isotype | Dilution | Source |
| --- | --- | --- | --- | --- |
| microglia | anti-Mac-1 | rat | 1:25 | Pharmingen |
| astrocytes | anti-GFAP | rabbit | 1:100 | Dako Inc. |
| CD4' T | anti-L3T4 | rat | 1:25 | Pharmingen |
| CD8' T | anti-Lyt 2.2 | rat | sup. | ATCC |
| NOS-2 | anti-iNOS | rabbit | 1:50 | Transduction Lab |
| NOS-3 | anti-ecNOS | rabbit | 1:50 | Transduction Lab |
| NOS-1 | anti-ncNOS | mouse | 1:50 | Transduction Lab |
| MHC I | 31.3.4s, 34.2.12s, 28.14.8, 28.13.3s, 28.8.6 | mouse | sup. | ATCC |
| MHC II | MKD6, 14.4.4s, 28.16.8s | mouse | sup. | ATCC |
| IFNγ-R | anti-GR20 | mouse | sup. | ATCC |
| IFN-γ | DB-1 | mouse | 1:100 | BioSource Int. |
| VSV | anti-VSV | sheep | 1:200 | E. O'Rourke |
| NK | NK1.1 | mouse | 1:50 | Pharmingen |

Most serological reagents used in this study are listed in Table 2. A mixture of mAbs 31.3.4s, 34.2.12, and 28.14.8 (specific for H-2K$^d$, D$^d$, and L$^d$, respectively) was used for staining MHC class I Ags. Mouse mAbs MK-D6 and 14.4.4 (H-2 I-A$^d$ and I-E$^d$, respectively) were pooled to detect MHC Class II expressing cells. Biotin-labeled secondary Abs specific for the species f the primary Abs and avidin-biotinylated horseradish peroxidase complex were purchased from Vector Laboratory (Burlingame, Calif.). 3,3'-Diaminobenzidine (DAB) and its diluting buffer were obtained from Calbiochem Corp. (San Diego, Calif.)

Immunohistochemical Staining

Brains were sectioned (20 μm sections) in the sagittal orientation using a cryostat: 20–30 serial sections of each brain were prepared on subbed slides. In each staining experiment, brain sections were removed from the freezer and warmed at room temperature for ten minutes before being fixed in 10% neutral buffered formalin for one minute. Sections were then washed twice in 0.1M Tris buffered saline (TBS, pH 7.6), ten minutes each. Endogenous peroxidase activity was blocked by incubating sections in 0.3% H$_2$O$_2$ in 0.1M TBS for 20 minutes. Sections were then washed twice in 0.1M TBS, and background staining was blocked by preincubation in 1% bovine serum albumin (BSA) (Fisher Scientific, Pittsburgh, Pa.) in 0.1M TBS for 45 minutes. Sections were then incubated with primary Abs for specific Ags for one hour at room temperature, except for VSV staining which was conducted overnight. Sections were washed again in 0.1M TBS twice and then incubated in biotinylated secondary Ab (ABC Kit, Vector Laboratory), followed by avidin-biotinylated peroxidase for another 30 minutes. Sections were then incubated with DAB in 0.01% H$_2$O$_2$ for five minutes. Dried sections were coverslipped with Permount (Fisher Scientific).

ELISA

ELISA procedures were essentially as described by the manufacturers. The Mouse IFN-γ ELISA kit was purchased from BioSource International (Camarillo, Calif.). The Mouse TNF-γ ELISA kit was purchased from Genzyme (Cambridge, Mass.)

Cells and Viruses.

NB41A3 neuroblastoma cells and C6 astrocytoma cells were obtained from ATCC. RAW murine macrophage cells were generously provided by Dr. Ashok Amin, Hospital for Joint Diseases, NYU. CHO cells, obtained from Dr. Alice S. Huang, were maintained as previously described (Huneycutt et al, 1994). The mouse hybridoma, GR-20, a mAb antagonist to the IFN-γR, was purchased from ATCC, as were the rat mAb XMG1.2 and GL113.

Plaque Assay of Infectious Viral Titer

Infectious virus was quantified on CHO cell monolayers. Monolayers were prepared by inoculating 20×10$^4$ cells in 1 ml per well (234-23ll plate, Nunc) and incubated for two days at 37° C. The medium was removed, 0.1 ml of each dilution of samples (ten-fold serial dilutions) was added to each well, in duplicate/triplicate, and the wells were then incubated for 30 minutes at 37° C. The medium was removed, 1 ml of the mixture of equal volumes of 1.8% agar (kept at 45° C.) and 2×culture medium (kept at 37° C.) were added to each well, and the wells were then incubated at 37° C. for 24 hours. Plaques were fixed with 10% formaldehyde for 30 minutes and stained with 0.5% methylene blue.

Chemicals and Cytokines

In some experiments, inhibitors of NOS were included. L-N-Methyl Arginine (L-NMA) (Sigma) and 7-nitroindazole (7-NI) (Calbiochem) were used at 400 μM as was the control compound, indazole (Aldrich). L- and D-arginine were purchased from Sigma and were used at 5 μM. Indomethacin was purchased from Sigma and was used at 10 μg/kg. Bayer Aspirin (ASA) was used at 100 mg/kg.

Recombinant mouse IFN-γ was purchased from Genzyme. Recombinant mouse IL-12 was provided by Genetics Institute. In some preliminary experiments, rat conA supernatant (Browning et al, 1990) was used as a source of IFN-γ; the validity of this assumption was tested using neutralizing mAb to IFN-γ or to its receptor.

Determination of NO Concentration

The concentration of NO in culture supernatants was determined by assaying its stable end-product, NO$_2$ (Bredt et al, 1989). Briefly, equal volumes of experimental sample and Griess reagent (1% sulfanilamidide, 0.1% N-1-naphthylethylene-diamine, 5H$_3$PO$_4$) (Sigma) were incubated at room temperature for ten minutes. The reaction produces a pink color, which was quantitated at 540 nm against standards in the same buffer, using an automated plate reader (Bio-Tek, Inc., model EL309). The data is expressed as mM.

Immunoprecipitation

NB41A3 cells (5×10$^5$) were cultured in culture medium with our without IFN-γ for 72 hours. Cells were mock infected with media or infected with VSV (1 MOI) for 2.5 hours or 5 hours. Cells were then chilled on ice for ten minutes and lysed with 0.5 mL of lysis buffer (0.5% NP-40, 300 mM NaCl, 50 mM Tris, 100 μg/ml PMSF, 1 μg/ml leupeptin, pH 7.4) for 20 minutes. Cell lysate was centrifuged at 12,000 g for two minutes. Equal amounts of supernatant (150 μl) were precleared with 50% protein A-sepharose 2–3 times. Sheep anti-VSV Ab was added to the cell lysate for one hour at 37° C. Protein A complex was pelleted down in a microfuge for one minute and boiled for five minutes in dissociation buffer (0.05% bromphenol blue, 0.0625 M Tris, 1% SDS, 10% glycerol, 1% 2-mercaptoethanol) before running on a 7.5% SDS-PAGE gel to be analyzed on a Western Blot.

Western Blot Protocol

NB41A3 cells (5×10$^5$) were cultured in culture medium with or without IL-12 for 72 hours. The cells were then either mock infected with medium or infected with VSV at 1 moi for 2.5 hours or 5 hours, upon which they were lysed with lysis buffer (0.5% NP-40, 300 mM NaCl, 50 mM Tris, 100 μg/ml PMSF, 1 μ/ml Leupeptin, pH 7.4. The proteins were run on a 7.5% SDS-PAGE gel and electrophoretically transferred onto a nitrocellulose membrane. After transfer, the blot was washed in PBS-0.05. Tween-20 for ten minutes. The blot was blocked using PBS containing 3% nonfat dry milk for 20 minutes. Anti-VSV Ab (1:5000) or anti-nitrotyrosine Ab (Upstate Biotechnology, NY) (1:10000) was added, and the incubation was carried out at room temperature for two hours. After washing the membrane with PBS, secondary antibody (anti-sheep for VSV, anti-rabbit for nitrotyrosine) at 1:3000 dilution for 1.5 hours at room temperature. The blot was incubated with Enhanced Chemiluminescence substrate (ECL) (Amersham) based on the manufacturer's directions. Film exposure was on Kodak Bio-Max MR film for two minutes. Phosphorimaging analysis of the gel was applied with Bio-Rad Model GS-250 Molecular Imager™.

PCR-Dig Labelling of the Probes

The plasmids encoding the five VSV proteins were generously provided by Dr. John Rose (Yale University) (Lawson et al, 1995). These clones were used to generate the probes for the Northern Blots. The PCR Dig Probe Synthesis Reaction (Boehringer Mannheim) was used to label the fragments. Briefly, this required two sets of PCR reactions. The first reaction generated a concentrated batch of double-stranded DNA encoding the region of interest. The second reaction generated single-stranded (either 5' or 3') Dig-labelled DNA fragments, which were used as probes. The reactions conditions were:

| Round 1 | | |
|---|---|---|
| 10x Buffer | 5.0 μL | PCR Program |
| 15 mN MgCL$_2$ | 5.0 μL | 1) 9400 2 min. |
| 5' Primer (1.5 μM) | 5.0 μL | 2) 55 cycles of: |
| 3' Primer (1.5 μM) | 5.0 μL | 94° C. 30 sec |
| Taq (5 U/μL) | 2.5 μL | 55° C. 30 sec |
| DNA (0.1 μg/μL) | 10.0 μL | 72° C. 90 sec |
| dH$_2$O | 12.5 μL | 3) 15° C. hold |
| Round 2 (Vials from Kit) | | |
| Vial 3 | 5.0 μL | PCR Program |
| Vial 2 | 5.0 μL | Same as Above |
| Primer (1.5 μM) | 10.0 μL | |
| Vial 1 | 0.75 μL | |
| DNA (0.1 μg/μL) | approx. 1.5–2 μL (around 50 ng) | |
| dH$_2$O | to 50 μL final volume | |

The following primers were used for the PCR reactions:
VSV-N gene (Base pairs 77–1136):
  5-GAGGATCCAGTGGAATACCCGGC (SEQ ID NO:1),
  3'-CTACACCAGCTTACCGAGCCTACC (SEQ ID NO:2);
VSV-P gene (Base pairs 47–759):
  5'-TCCTATTCTCGTCTAGATCAGGCG (SEQ ID NO:3),
  3'-TATTTCTCCGGTAGGACGAGCCAG (SEQ ID NO:4);
VSV-M gene (Base pairs 94–798):
  5'-AGAAATTAGGGATCGCACCACCCC (SEQ ID NO:5),
  3'-CAGAGAGGATTAAGGTCGGAGAGC (SEQ ID NO:6);
VSV-G gene (Base pairs 211–1400):
  5'-TGCCCAAGAGTCACAAGGCTATTCA (SEQ ID NO:7),
  3'-GGTTAGCTGAAACAGCTTCCAACC (SEQ ID NO:8);
VSV-L gene (Base pairs 377–1399):
  5'-TGTAAACTGCACCACCTCTGGAAC (SEQ ID NO:9),
  3'-GGGCTGAATGATCTGGGTAGCTAT (SEQ ID NO:10).

Northern Blot Protocol

NB41A3 cells (5×10$^5$) were cultured in culture medium with or without IL-12 for 72 hours. The cells were then infected with VSV or mock infected with medium for one hour, upon which they were lysed using the Poly(A) pure mRNA purification kit (Ambion). The mRNA were run on 2% formaldehyde/agarose gel and transferred onto a nylon membrane. After transfer, the membrane was cross-linked using a UV Crosslinker (Stratagene). The membrane was then incubated in pre-hybridization buffer for two hours at 40° C. and hybridized overnight with the probes at the same temperature.

After the stringency washes, the signals were detected using the BM Genius 7 Kit (Boehringer Mannheim). Briefly, the membrane was incubated in blocking solution for 30 minutes. The membrane was then incubated with anti-dig/alkaline phosphatase conjugated antibody solution for 30 minutes. After the washes, the membrane was incubated with CSPD, which reacts with the alkaline phosphatase.

Transmission Electron Microscope (TEM) Tissue Preparation

Normal male BALB/c mice and NOS-3 KO mice, 5–7 weeks of age were used for this experiment. Some mice were intranasally infected with 2×10$^5$ PFU of VSV and injected with either 200 ng of IL-12 or medium alone daily until the time of sacrifice. Some uninfected mice were treated with IL-12 or medium. After a lethal dose of ketamine-xylazine, the mice were perfused with 5 mL of 0.9% saline/1% heparin solution, then with 200 mL of 2% paraformaldehyde/2% gluteraldehyde solution. After the brains were extracted, they were post-fixed over night in 2% paraformaldehyde/2% gluteraldehyde solution. The brains were sectioned coronally (50 μM) using a vibrotome, and the sections were placed in 0.1M PBS. The sections were then fixed in 1% OSO$_4$ for one hour. The tissues were dehydrated sequentially with:
  (1) 30% EtOH, twice for five minutes each;
  (2) 50% EtOH, once for five minutes;
  (3) 4% uranyl acetate (in 70% EtOH for one hour;
  (4) 90% EtOH, once for five minutes;
  (5) 100% EtOH, twice for ten minutes each;
  (6) 100% acetone, three times for ten minutes each.

After dehydration, the tissues were placed into 1:1 (epon:acetone mixture) for two hours. The epon concentration was as follows: EM-Bed 812 (24 mL), DDSA (15 ml), NMA (13.5 mL), and DMP (0.525 mL). After two hours, the tissues were placed in full epon for two more hours with gentle agitations. The tissue was flat embedded onto clean aclar sheets and baked overnight in an oven at 65° C. until the epon was fully polymerized. Of the prepared tissue, an area of interest was cut out and placed onto an epon block for sectioning on the ultramicrotome to a thickness of approximately 900 angstroms. These sections were then transferred to copper grids and stained with lead citrate for one minute before transferring them to the TEM.

Results

IFN-γ Treatment Significantly Increases NB41A3 cells' Production of NO

Figure 2A:
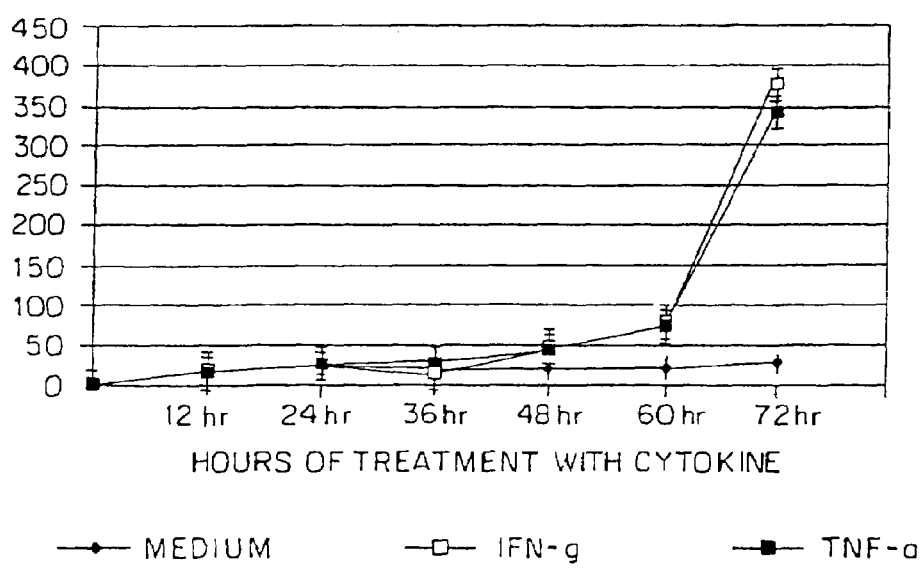
FIGS. 2A–2C show the kinetics of the IFN-γ augmented NOS activity in NB41A3 neuroblastoma, C6 rat glioma and RAW cells. Aliquots of supernatant were removed from triplicate wells of $2\times10^5$ NB41A3 (FIG. 2A), RAW (FIG. 2B) or C6 (FIG. 2C) cells, cultured with medium or with 5 ng IFN-γ for up to 72 hours. The medium was assayed for the presence of $NO_2$ using the Griess reagent, and expressed as nM $NO_2$ ±S.D. present.
Figure 2B:
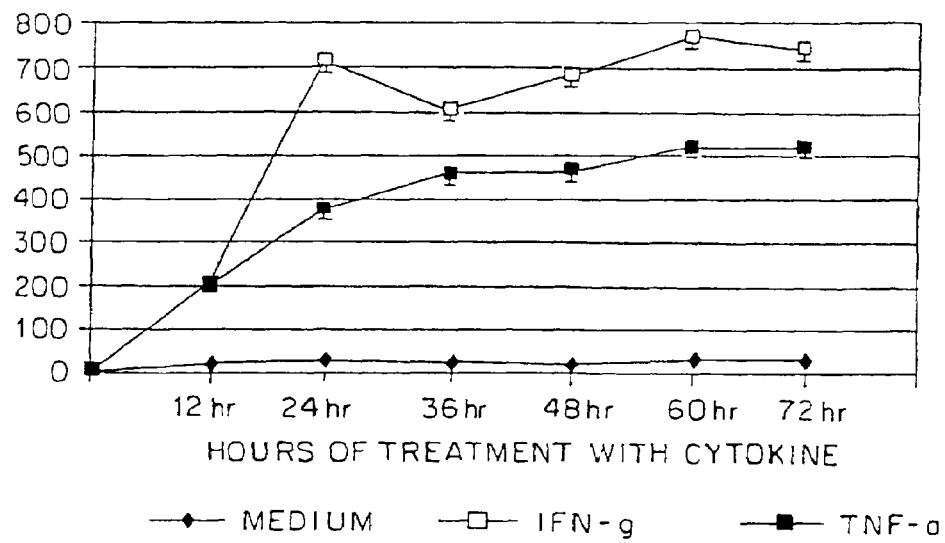
Figure 2C:
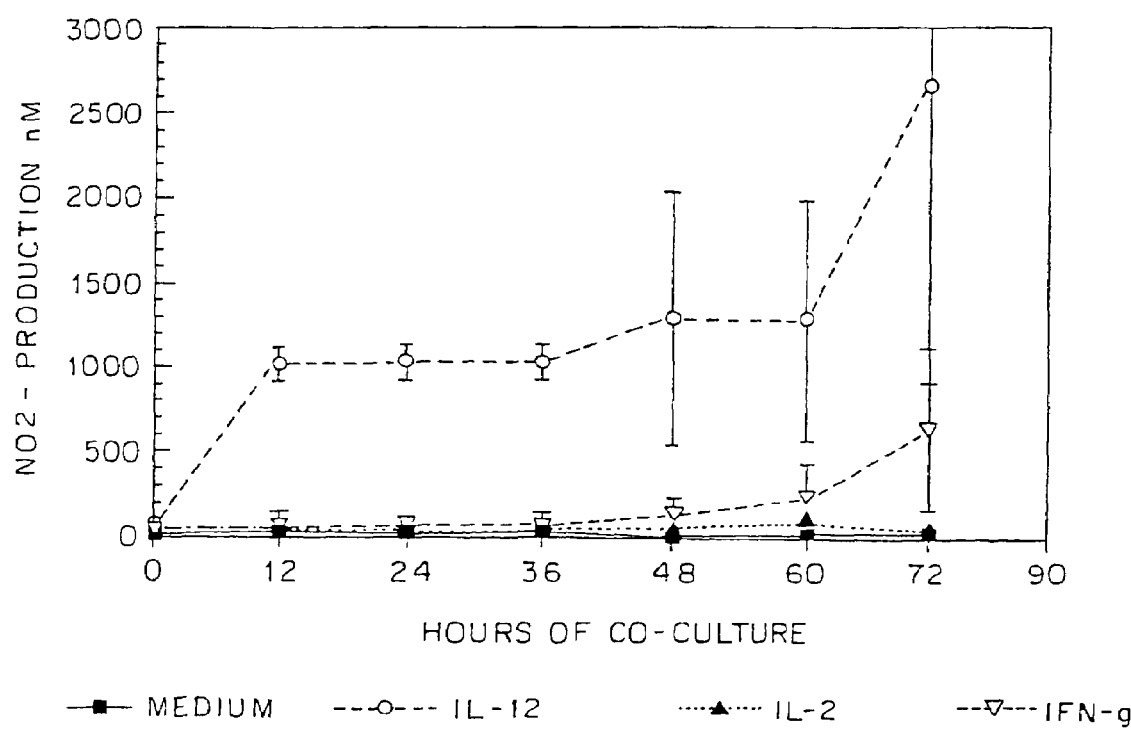

NO production by NB41A3 cells was significantly increased by IFN-γ as was observed previously with astrocytes and endothelial cells (Barna et al, 1996). The kinetics of induction of $NO_2$ secretion into the cell culture medium was examined, contrasting the neuroblastoma cells with a murine macrophage line, RAW, frequently used to study Type II NOS. FIGS. 2A–2C show the release of $NO_2$ from each source. The macrophage line reaches plateau levels of production by 24 hours of incubation with 5 ng rIFNγ (FIG. 2B). Neuroblastoma cells and astrocytes do not reach substantial levels of $NO_2$ production until 72 hours of co-culture (FIGS. 2A and 2C, respectively).

7-NI Treatment of Mice Alters the Course of Viral Replication in the CNS

Figure 3:
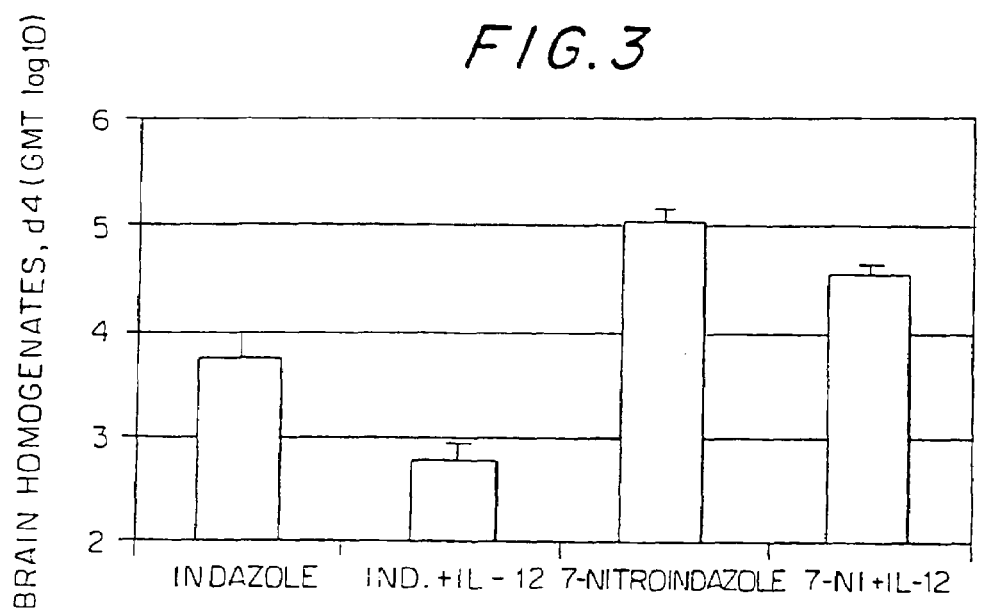
FIG. 3 shows the role of type 1 NOS in IL-12 inhibition of VSV in vivo. Four groups of 10 mice each were injected with 50 mg/kg Indazole or with 7-NitroIndazole and medium (hatched bars) or with 200 ng IL-12 (cross-hatched bars) and were infected intranasally with $2\times10^5$ PFU VSV. At four days post infection, mice were sacrificed and brain homogenates were prepared. The amount of virus in individual samples was determined by plaque assay on CHO monolayers. Geometic mean titers ±SEM are shown.

To determine whether type I NOS activity was biologically relevant in the CNS of mice infected intranasally, groups of BALB/c male mice were infected with VSV and were injected with either indazole or with 7-NI. In addition, half of the mice were injected with IL-12, which was shown by the laboratory of the present inventors to have profound recovery-promoting effect(s) in this experimental system. Four days later, the mice were sacrificed, and brain homogenates were tested for the presence of virus. FIG. 3 shows the results of the plaque assay on homogenates. The geometric mean titer (GMT) of virus in individuals within each group was compared. 7-NI treatment of mice resulted in a ten-fold greater GMT compared to indazole-treated mice. In addition, 7-NI treatment abrogated the IL-12-mediated enhanced clearance of VSV (FIG. 3). This is consistent with our hypothesis that IL-12 induced IFN-γ, which in turn stimulated NOS in the CNS. These data clearly demonstrate the substantial contribution of type I NOS to restricting viral replication within neurons of the CNS during experimental VSV infection.

IFN-γ Induced Upregulation of Type I NOS Activity Inhibits VSV Replication

Whether viral replication in NB41A3 cells could be inhibited by IFN-γ-induced type I NOS was investigated. Treatment of NB41A3 cells for 72 hours prior to infection significantly inhibited VSV and HSV-1 replication (Table 3). Replication of influenza virus A/WSN/33 and Sindbis virus in NB41A3 cells was also significantly inhibited. In other experiments, the IFN-γ-mediated reduction in viral propagation was prevented by addition of anti-IFN-γR mAb GR-20 (results not shown). The abrogation of IFN-γ-induced inhibition of VSV and HSV-1 replication by the L-arginine analogues L-NMA and 7-NI suggest that the IFN-γ-induced inhibition is due to type I NOS activity. In contrast, while IFN-γ treatment inhibited influenza and Sindbis virus replication, this was not reversible with arginine analogues. The data suggest that influenza is susceptible to other IFN-γ-induced anti-viral enzymes (Staeheli, 1990), but not to NO-mediated inhibition.

TABLE 3

Interferon-γ-Induced Viral Inhibition in NB41A3 Cells
Growth of VSV and HSV-1 is sensitive to nitric oxide-mediated inactivation, but influenza and Sindbis viruses are resistant to NOS-inhibition

|  | VSV | | Influenza | | Sindbis | | HSV-1 | |
|---|---|---|---|---|---|---|---|---|
| Inhibitor* | Media | IFN-γ | Media | IFN-γ | Media | IFN-γ | Media | IFN-γ |
| Media | 5.615 ± .282 | 3.752 ± .034 | 5.683 ± .140 | 3.810 ± .130 | 4.859 ± .089 | 3.318 ± .373 | 5.016 ± .176 | 3.467 ± .408 |
| 7-NI | 5.985 ± .428 | 5.752 ± .331 | 5.560 ± .489 | 3.897 ± .089 | 4.935 ± .056 | 3.897 ± .089 | 5.159 ± .194 | 5.170 ± .264 |
| Indazole | 5.460 ± .408 | 3.678 ± .174 | 5.268 ± .350 | 3.546 ± .212 | 5.053 ± .217 | 3.752 ± .046 | 5.140 ± .204 | 3.175 ± .369 |
| L-NMA | 5.948 ± .089 | 5.761 ± .151 | 5.810 ± .131 | 3.767 ± .208 | 5.033 ± .238 | 3.796 ± .084 | 5.359 ± .225 | 5.227 ± .208 |

*Cultures of NB41A3 cells were stimulated with media or 5 μg IFN-γ for 72 hours prior to 8 hour infection with VSV, A/WSN/33. Sindbis AR339, or HSV-1 at a moi = 1; in some cultures NOS inhibitors 7-NI and L-NMA were added at 400 mM. Supernatants were assayed for infectious virus on NB41A3 monolayers.
Data is expressed as Log10 PFU ± SD.
Underlined data is significantly different from control values; P < .001.

Inhibition of VSV Replication in NB41A3, but Not RAW and C6 Cells is Attributable to Type I NOS Activity 7-Nitroindazole (7-NI) is a selective inhibitor of type I, but not types II or III NOS (Moore et al, 1993). Therefore, cells expressing the three isoforms of NOS were incubated with IFN-γ, NMDA or medium and two inhibitors, L-NMA and 7-NI, and the cells were infected with VSV, and the progeny virus was determined eight hours later by plaque assay. L-NMA antagonized NOS-associated inhibition of viral replication in all three cell lines, whether NOS activated by triggering of the cells through their glutamate receptors, or by IFN-γ treatment (Table 4). 7-NI treatment was controlled with indazole incubation. Only neuronal NOS was antagonized with 7-NI, the resultant virus produced in RAW and C6 cells was indistinguishable from medium- or indazole-treated activated cells.

TABLE 4

VSV Infection in the Presence of NOS Inhibitors

| Cells | Inhibitor/Treatment | Medium | NMDA | IFN-γ |
|---|---|---|---|---|
| RAW | Medium | 5.79 ± .09 | — | 4.55 ± .49 |
| RAW | 7-NI | 5.87 ± .08 | — | 4.84 ± .15 |
| RAW | L-NMA | 5.83 ± .13 | — | 5.71 ± .09 |
| RAW | Indazole | 5.45 ± .21 | — | 4.49 ± .48 |
| NB41A3 | Medium | 5.80 ± .10 | 3.71 ± .20 | 3.94 ± .06 |
| NB41A3 | 7-NI | 5.76 ± .18 | 5.57 ± .15 | 5.76 ± .10 |
| NB41A3 | L-NMA | 5.76 ± .25 | 5.59 ± .27 | 5.77 ± .21 |
| NB41A3 | Indazole | 5.58 ± .27 | 4.39 ± .36 | 4.23 ± .29 |

TABLE 4-continued

VSV Infection in the Presence of NOS Inhibitors

| Cells | Inhibitor/ Treatment | Medium | NMDA | IFN-γ |
|---|---|---|---|---|
| C6 Glia | Medium | 5.89 ± .21 | 5.54 ± .24 | 4.41 ± .37 |
| C6 Glia | 7-NI | 5.83 ± .14 | 4.59 ± .52 | 4.54 ± .14 |
| CG Glia | L-NMA | 5.85 ± .08 | 5.38 ± .37 | 5.59 ± .26 |
| C6 Glia | Indazole | 5.63 ± .19 | 4.48 ± .17 | 4.48 ± .42 |

In Vitro Conditions: Inhibitors were used at 400 mM, NMDA at 500 mM for two minutes, IFN-γ at 5 ng for 72 hours, initial infection moi = 1, data shown is $\log_{10}$ PFU virus ±SD derived from supernatants harvested 8 h pi. Underlined data points are significantly different from uninhibited viral replication, P < .05 or better.

Figure 4:
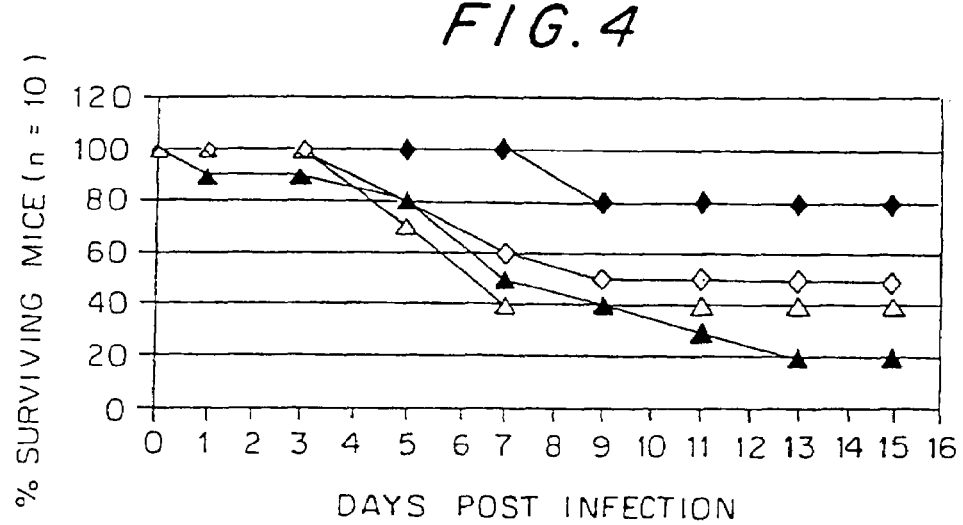
FIG. 4 demonstrates how IL-12 treatment increased survival from VSV infection. Groups of ten mice were injected i.p. with either the control medium or 200 ng IL-12 on days 0–7 post infection. All mice were infected intranasally with VSV ($2\times10^5$ PFU/10 μL). The number of survivors was greater in mice treated with IL-12 in WT mice but not in NOS-1 KO mice.
Figure 5:
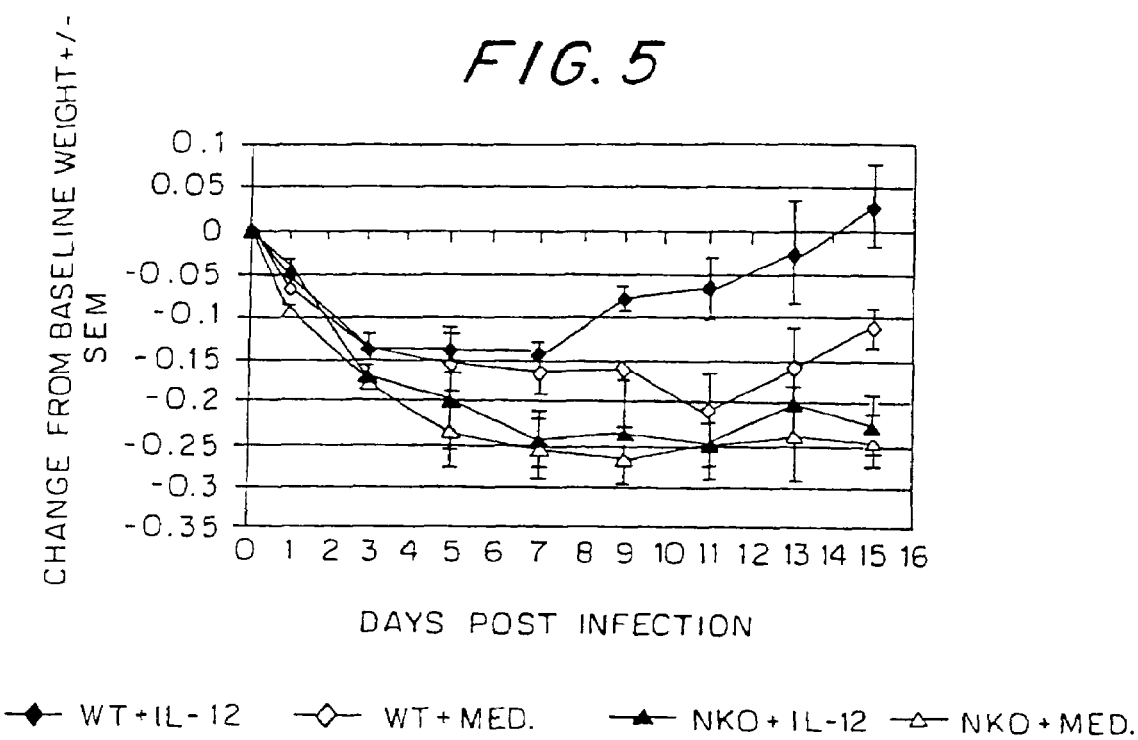
FIG. 5 shows that IL-12 significantly increased weight loss recovery from VSV infection. The average weight ±SEM of the surviving mice from FIG. 4 was recorded. Mice receiving IL-12 treatment were found to rapidly recover from the weight loss from the viral infection, as determined by the Student's t test in WT mice but not in NOS-1 KO mice.

Morbidity and Mortality: IL-12 Treatment Resulted in Increased Survival and More Rapid Recovery from Weight Loss IL-12 treatment resulted in twice the survival rate from VSV infection in WT mice than observed in control mice (FIG. 4). Initially, both groups of VSV-infected mice lost weight. IL-12-treated mice rapidly gained weight and exceeded their initial measures by 12 days after infection, while the control infected mice showed more signs of morbidity (decreased appetite and activity) and remained below the initial level throughout the two-week observation period (FIG. 5). IL-12 treatment was not able to rescue the NOS-1 KO mice, suggesting that NOS-1 is important for host defense (FIGS. 4 and 5).

Figure 6:
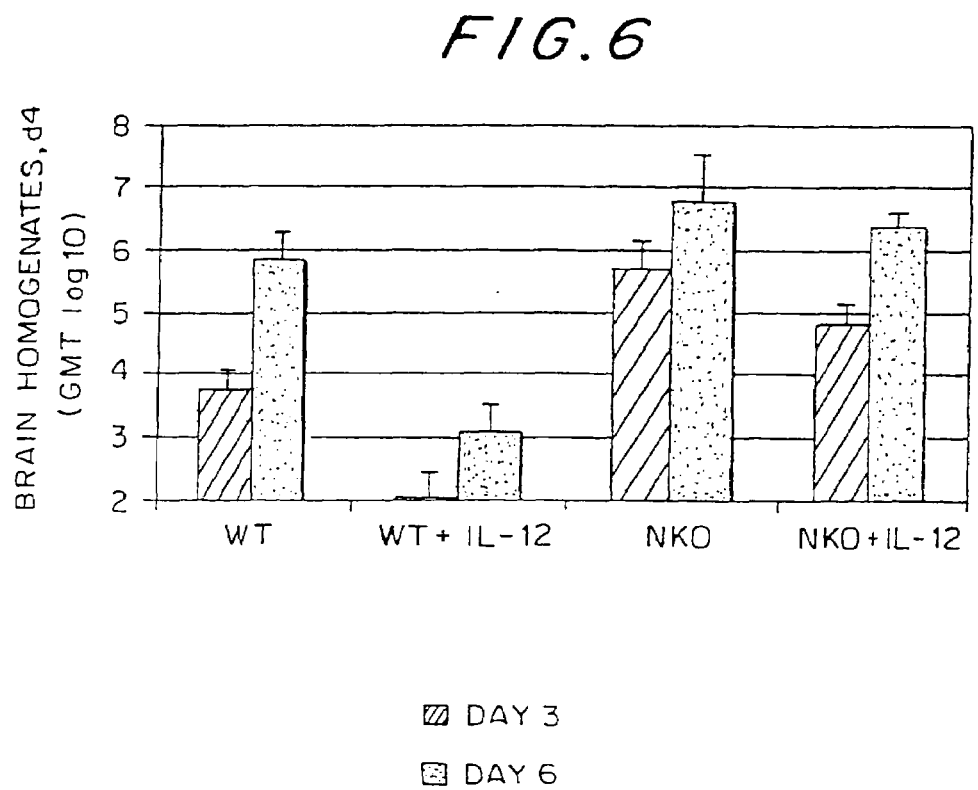
FIG. 6 shows that IL-12 treatment significantly inhibited VSV infection in the CNS. Groups of six mice were injected i.p. with either the control medium or 200 ng IL-12 on days 0–4 post infection. All mice were infected intranasally with VSV ($2\times10^5$ PFU/10 μL). On day four post infection, six mice of each group were sacrificed, and the mouse brains were homogenized for determination of viral titers on CHO cells. Viral titers of mice receiving IL-12 treatment were found to be significantly lower than those of the control mice, as determined by the Student's t test (P<0.01).
Figure 7A:
FIGS. 7A–7D show the IL-12 treatment-enhanced expression of NOS-1. Serial sections of three mouse brains from each treatment group were removed at day four post infection and stained with anti-bNOS Ab. The olfactory bulb region shows NOS-1 immunoreactivity in the WT medium group (FIG. 7A; bar=15 nM), the IL-12 treated WT group (FIG. 7B; bar=15 nM), the NOS-1 KO medium group (FIG. 7C; bar=15 nM), and the IL-12 treated NOS-1 KO group (FIG. 7D; bar=15 nM).
Figure 7C:
Figure 7B:
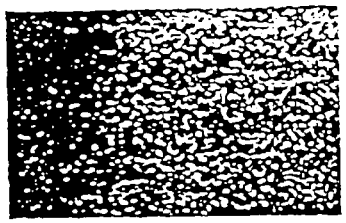
Figure 7D:

IL-12 Treatment Decreased VSV Titers in the Brain Homogenates, but not in the NOS-1 Knockout Mice The viral titers of mice treated with IL-12 were lower in WT, but not in NOS-1 KO mice, than the control groups (FIG. 6). Injection of 200 ng of IL-12/mouse per day decreased the VSV titer about 100-fold for the WT mice. Immunohistochemical staining of VSV Ags on frozen sections from brains of other mice confirmed this observation.

IL-12 Treatment Enhanced the Expression of Both MHC Class I and Class II Ags

Neither uninfected B6 WT nor NOS-1 KO brain sections expressed MHC Ags above the background level of immunohistochemical staining. However, four days following VSV infection, expression of MHC class I was observed in the olfactory bulb (OB) of all groups (Tables 5A and 5B). Strongest staining of MHCV class I coincided with VSV Ag areas. Induced expression of MHC class II was barely detected in the OB in the control groups, consistent with our earlier observations (Christian et al, 1996).

Following IL-12 treatment, expression of MHC Ags was significantly increased in both the wild-type and the knock-out groups. MHC class I Ags was found in the OB, the hippocampal formation, and along the fourth ventricle. Expression of MHC class II Ags was increased in many areas, particularly in the OB and the hippocampal formation (Tables 5A and 5B). In the absence of NOS-1, MHC was induced well above baseline levels, though it was lower than that of IL-12 treated WT mice.

IL-12 Treatment Induces Activation of Astrocytes and Microglia

The brain sections were stained for either glial fibrillary acidic protein (GFAP), a marker of astrocytes, or Mac-1 Ag expressed by microglial cells. IL-12 Treatment resulted in more numerous and heavier-staining cells, suggesting astrocytosis and microgliosis (Tables 5A and 5B). The most pronounced astrocytosis and microgliosis was observed to coincide with VSV Ag$^+$ areas.

TABLE 5A

IL-12 Treatment Induces CNS Parenchymal Changes in Both WT and NOS-1 KO Mice

| | Infected | | | | | | | | | | | |
|---|---|---|---|---|---|---|---|---|---|---|---|---|
| | WT | | | WT + IL-12 | | | NOS-1 KO | | | NOS-1 KO + IL-12 | | |
| Antigen | OB | HC | FV | OB | HC | FV | OB | HC | FV | OB | HC | FV |
| VSV | +++ | ++ | ++ | + | + | + | +++ | ++ | ++ | +++ | ++ | ++ |
| MHC-I | + | + | − | +++ | +++ | ++ | + | − | − | ++ | ++ | + |
| MHC-II | + | − | − | ++ | +++ | + | + | − | − | ++ | + | + |
| GFAP | 285 ± 9.5 | 96 ± 3.5 | 46.0 ± 5.7 | 395 ± 11.5 | 176 ± 21.5 | 76.0 ± 4.5 | 208 ± 11.5 | 71.0 ± 6.5 | 30.5 ± 11.0 | 145 ± 24.7 | 121 ± 13.0 | 60.0 ± 11.3 |
| Mac-1 | 30.0 ± 5.5 | 9.0 ± 1.5 | 10.0 ± 2.5 | 55.0 ± 5.0 | 28.0 ± 4.5 | 25.0 ± 3.5 | 17.0 ± 2.0 | 7.5 ± 2.1 | 4.0 ± 0.0 | 33.3 ± 3.1 | 21.5 ± 6.1 | 14.5 ± 5.1 |
| NOS-1 | 11.0 ± 3.5 | 22.0 ± 2.5 | 9.0 ± 2.0 | 32.0 ± 3.5 | 40.0 ± 2.5 | 20.0 ± 3.0 | 4.0 ± 2.5 | 3.0 ± 1.0 | 3.0 ± 1.5 | 6.5 ± 2.5 | 7.3 ± 3.1 | 6.5 ± 2.5 |
| NOS-2 | 48.0 ± 5.0 | 25.0 ± 2.0 | 25.0 ± 4.5 | 128 ± 18.0 | 65.0 ± 9.5 | 95.6 ± 4.5 | 39.0 ± 6.1 | 23.5 ± 2.5 | 25.0 ± 4.1 | 57.5 ± 4.5 | 41.5 ± 9.8 | 37.0 ± 8.0 |
| NOS-3 | 21.0 ± 2.5 | 15.0 ± 4.0 | 5.0 ± 1.7 | 59.0 ± 7.6 | 40.0 ± 2.0 | 20 ± 3.8 | 15.0 ± 2.8 | 14.5 ± 3.0 | 4.0 ± 1.4 | 38.3 ± 9.6 | 21.8 ± 3.6 | 9.6 ± 4.2 |
| NK1.1 | 26.0 ± 4.0 | 30.0 ± 6.5 | 30.0 ± 3.8 | 68.0 ± 4.3 | 68.0 ± 6.0 | 48.0 ± 6.5 | 30.5 ± 2.1 | 31.5 ± 6.4 | 20.5 ± 3.8 | 46 ± 3.8 | 41.0 ± 4.3 | 32 ± 3.2 |
| T cells | 26.5 ± 2.0 | 6.0 ± 2.0 | 1.0 ± 0.8 | 55.0 ± 8.1 | 22.0 ± 2.1 | 11.0 ± 1.5 | 30.0 ± 2.0 | 8.0 ± 1.4 | 3.0 ± 1.7 | 33.0 ± 7.1 | 14.8 ± 3.3 | 8.0 ± 2.1 |

TABLE 5B

IL-12 Treatment Induces CNS Parenchymal Changes in Both WT and NOS-1 KO Mice

| | Uninfected | | | | | | | | | | | |
|---|---|---|---|---|---|---|---|---|---|---|---|---|
| | WT | | | WT + IL-12 | | | NOS-1 KO | | | NOS-1 KO + IL-12 | | |
| | OB | HC | FV | OB | HC | FV | OB | HC | FV | OB | HC | FV |
| VSV | − | − | − | − | − | − | − | − | − | − | − | − |
| MHC-I | − | − | − | ++ | ++ | − | − | − | − | ++ | + | − |
| MHC-II | − | − | − | ++ | ++ | − | − | − | − | ++ | + | − |
| IFN-R | − | − | − | ++ | ++ | + | − | − | − | ++ | ++ | − |
| IL-12 | − | − | − | + | ++ | − | − | − | − | + | + | − |
| GFAP | 165 | 168 | 120 | 270 | 300 | 200 | 110 | 120 | 90 | 210 | 200 | 130 |
| Mac-1 | 10 | 7 | 6 | 18 | 10 | 15 | 9 | 9 | 9 | 13 | 14 | 13 |
| NOS-1 | 4 | 4 | 3 | 9 | 6 | 3 | 3 | 1 | 3 | 2 | 6 | 3 |
| NOS-2 | 20 | 10 | 10 | 30 | 25 | 15 | 18 | 10 | 9 | 26 | 21 | 14 |
| NOS-3 | 12 | 10 | 5 | 20 | 12 | 12 | 10 | 7 | 3 | 15 | 11 | 9 |
| NK1.1 | 3 | 6 | 5 | 10 | 7 | 9 | 4 | 4 | 5 | 9 | 8 | 10 |
| T Cells | 3 | 1 | 1 | 0 | 4 | 3 | 3 | 1 | 2 | 2 | 3 | 3 |

Tables 5A and 5B: Sagittal sections of the three mouse brains of each group removed on day four post infection were stained with the respective antibodies. Positively stained cells (GFAP, Mac-1, NOS-1, NOS-2, NOS-3, NK1.1 and T cells) were counted under a light microscope. Relative intensity (VSV, MHC-I, MHC-II and IL-12) of staining in specific areas was examined and expressed at four different levels: − = no visual staining; + = minimal staining; ++ = moderate staining; +++ = strong staining (as previously characterized in Bi et al (1995b) and Christian (1996)). OB = olfactory bulb; HP = hippocampus. Underlined data has been shown to be statistically different, as described by Student's t test, $P < 0.05$.

IL-12 Treatment Induces NOS-1, NOS-2 and NOS-3 Expression

NOS-1 expression was poorly detected in neurons in the uninfected and control groups, as previously observed by Komatsu et al (1996). Following IL-12 treatment, the expression was substantially increased in WT, but was undetectable in NOS-1 KO mice (Tables 5A and 5B, FIGS. 7A–7D).

NOS-2 expression by microglia and macrophates was found at low levels in the uninfected and control groups, consistent with previous data (Bi et al, 1994; Bi et al, 1995b). IL-12 treatment resulted in higher NOS-2 expression in both WT and NOS-1 KO mice (Tables 5A and 5B); lower in NOS-1 KO mice.

Expression of NOS-3 was previously observed in astrocytes and endothelial cells (Barna et al, 1996). IL-12 treatment induced the expression of NOS-3 in both WT and NOS-1 KO mice, although it was lower in NOS-1 KO mice (Tables 5A and 5B).

Infiltration of VSV Infected Brains by T Cells and NK Cells

T cells were detected very infrequently in media-treated infected B6 and uninfected B6 mouse brains. IL-12 treatment resulted in the accumulations of CD4 and CD8 expressing T cells in the VSV-infected areas, such as the OB and HC (Tables 5A and 5B).

NK1.1 expressing cells were detected at relatively higher frequency in the infected media-treated than in uninfected brains (Tables 5A and 5B). A profound increase in the number of NK cells was found in the OB and other areas following L-12 treatment in both WT and NOS-1 KO sections.

Viral Protein Production

Figure 8:
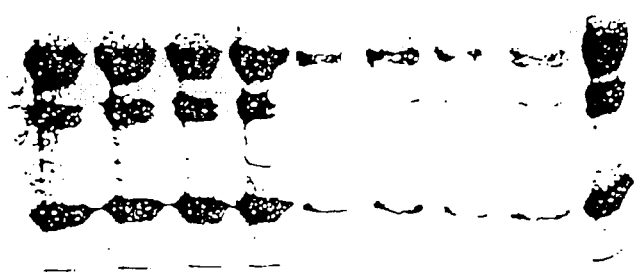
FIG. 8 shows that the levels of VSV protein production is inhibited in cells treated with IL-12. Cultures of NB41A3 cells were stimulated with media or 5 ng of IL-12 for 72 hours prior to 2.5 or 5-hour infection with VSV at 1 moi. Cells were lysed and the proteins were run on 7.5% SDS-acrylamide gel and a Western Blot was performed.
Figure 9:
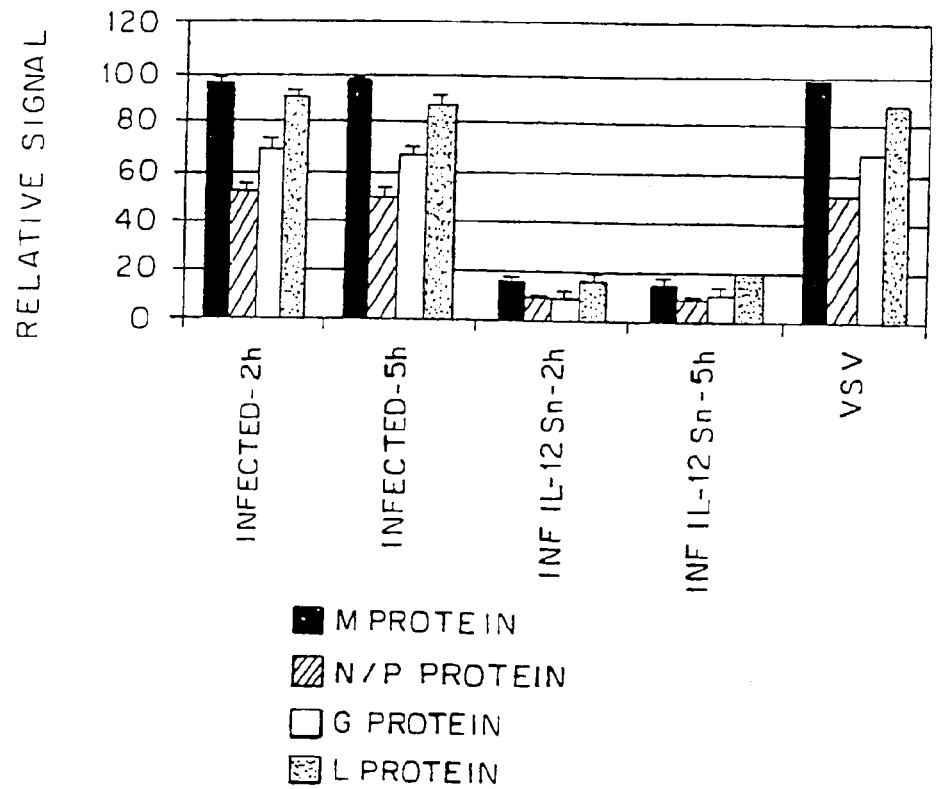
FIG. 9 shows the relative density levels of VSV protein production. The relative density of the bands from FIG. 8 was measured. The data reveals there is an approximately 80% difference in the relative amounts of viral protein between the treated and untreated samples.

The laboratory of the present inventors investigated whether viral replication in NB41A3 cells for 72 hours prior to infection significantly inhibited VSV protein replication (FIGS. 8 and 9). Analysis of the data revealed an approximately 80% difference in the relative amounts of viral protein between the treated and the untreated samples. These results were consistent at both 2.5 hours and 5 hours post infection and were uniform for each of the five viral proteins. The VSV control showed protein levels similar to those of the untreated samples.

Levels of Nitrosylation

Figure 10:
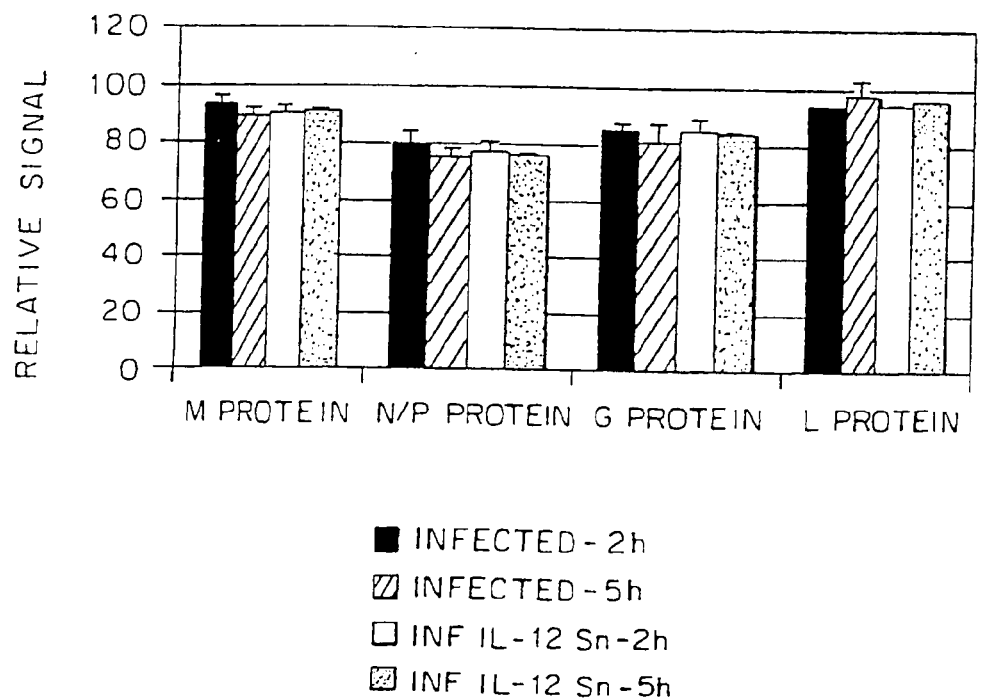
FIG. 10 shows that the VSV proteins are nitrosylated. Cultures of NB41A3 cells were stimulated with media or 5 ng of IL-12 for 72 hours prior to 2.5 to 5-hour infection with VSV at 1 moi. Cells were lysed and the VSV proteins were immunoprecipitated and run on a 7.5% SDS-acrylamide gel. The levels of nitrosylation was similar in all of the samples, even though the samples treated with cytokines contained much less viral protein.

To determine whether the viral proteins from the above samples are nitrosylated, the viral proteins were immunoprecipitated, and a Western Blot was run for α-Nitrotyrosine residues. The levels of nitrosylation in all of the samples were found to be very similar, even though the samples treated with cytokines contained much less viral protein (FIG. 10). As in the previous experiment, the results were consistent at both 2.5 hours and 5 hours post infection and were uniform for each of the five viral proteins.

Simultaneously Stained Gels

The gels stained simultaneously showed results which were consistent with the previous two experiments (FIGS. 9 and 10). There was a significant difference in viral protein levels between treated and untreated samples, and the levels of nitrosylation in all of the samples were very similar.

Viral mRNA Production

Figure 12:
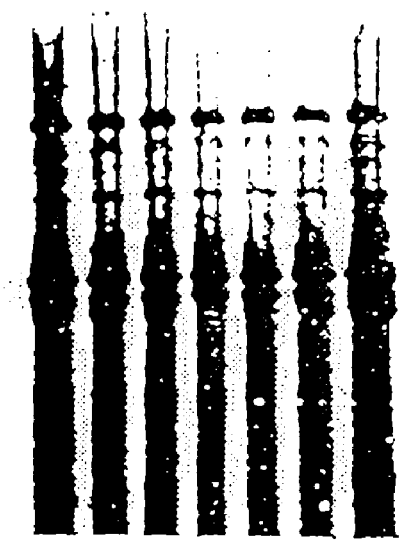
FIG. 12 shows that the levels of VSV mRNA production is inhibited in cells treated with IL-12. Cultures of NB41A3 cells were stimulated with media or 5 ng of IL-12 for 72 hours prior to one-hour infection of VSV at 1 moi. Cells were lysed and the mRNA were run on 2% agarose/formaldehyde gel and a Northern Blot was performed for the mRNA encoding the N gene.
Figure 13:
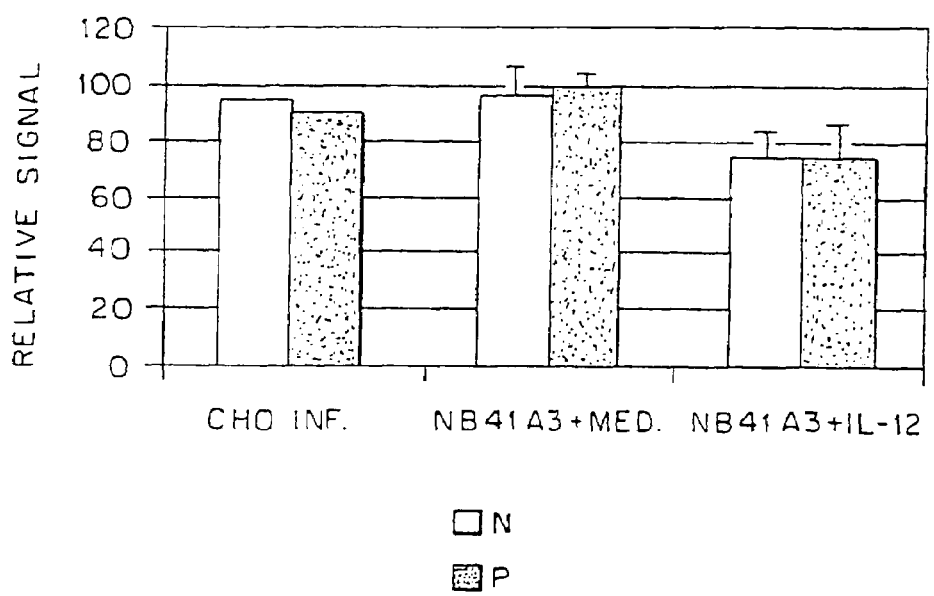
FIG. 13 shows the relative density levels of VSV mRNA production. The relative density of the bands from FIG. 12 was measured. The data reveals that there is an approximately 20% difference in the relative amounts of viral mRNA between the treated and untreated samples.

Whether viral replication in NB41A3 cells could be inhibited by IL-12-induced type I NOS was investigated. Treatment of NB41A3 cells for 72 hours prior to infection significantly inhibited VSV mRNA transcription (FIGS. 12 and 13). Analysis of the data revealed an approximately 20% difference in the relative amounts of viral mRNA between the treated and untreated samples. These results were consistent with the observations from FIGS. 8–11.

Figure 14:
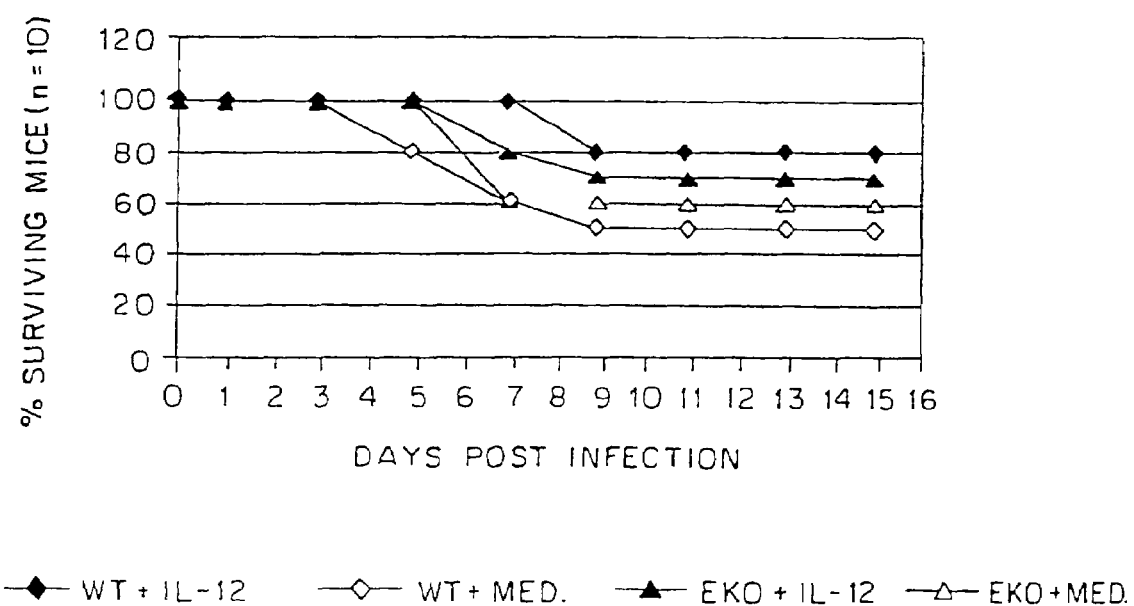
FIG. 14 shows that IL-12 treatment increased survival from VSV infection. Groups of ten mice were injected i.p. with either the control medium or 200 ng IL-12 on days 0–7 post infection. All mice were infected intranasally with VSV ($2 \times 10^5$ PFU/10 $\mu$L). The number of survivors was greater in mice treated with IL-12, even in the NOS-3 KO mice.
Figure 15:
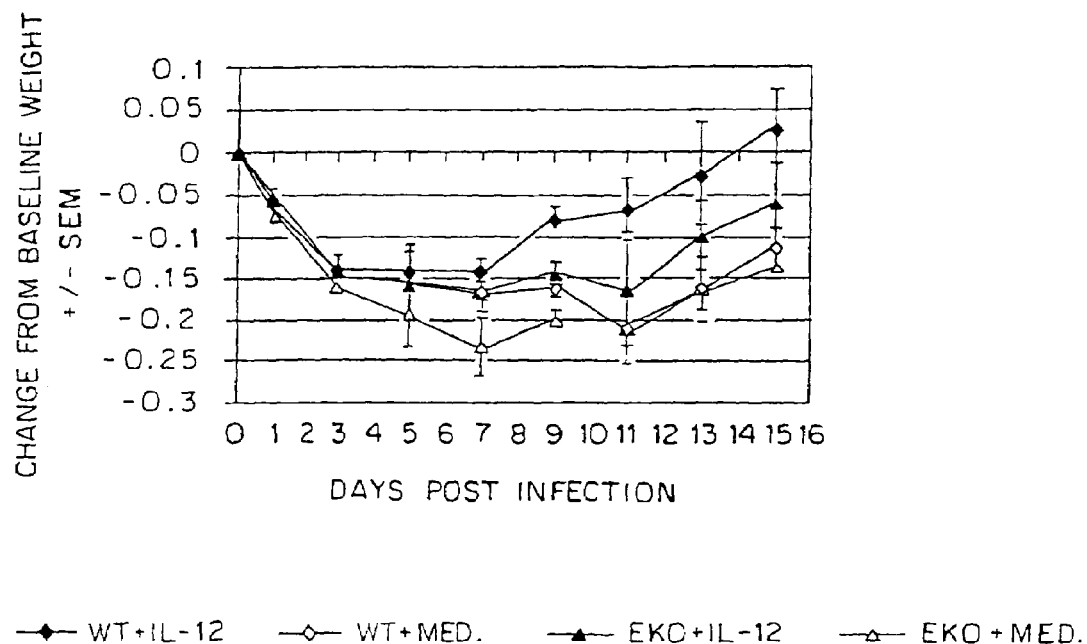
FIG. 15 shows that IL-12 treatment significantly increased weight loss recovery from VSV infection. The average weight, ±SEM, of the surviving mice from FIG. 14 was recorded. Mice receiving IL-12 treatment were found to rapidly recover from the weight loss from the viral infection, as determined by the Student's t test, even in NOS-3 KO mice.

Morbidity and Mortality: IL-12 Treatment Resulted in Increased Survival and More Rapid Recovery from Weight Loss IL-12 treatment resulted in twice the survival rate from VSV infection than observed in control mice (FIG. 14). Initially both groups of VSV-infected mice lost weight. IL-12-treated mice rapidly gained weight and exceeded their initial measurements by 12 days after infection, while the control infected mice showed more signs of morbidity (decreased appetite and activity) and remained below the initial level throughout the two-week observation period (FIG. 15). This suggests that IL-12 treatment was associated with an acute and transient cytokine-induced physiological response, possibly due to increased cytokine levels, such as TNF-α (see below), which resulted in weight loss. The control group lost weight as a result of their acute infection (Komatsu et al, 1996; Plakhov et al, 1995).

Figure 16:
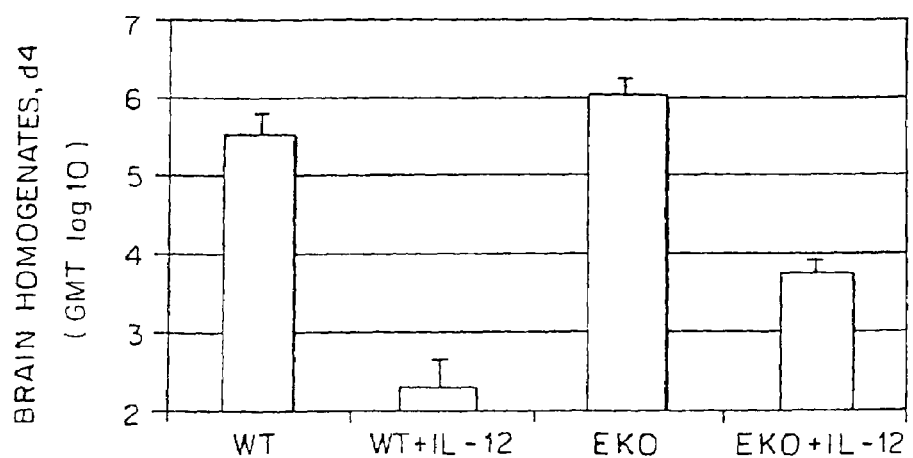
FIG. 16 shows that IL-12 treatment significantly inhibited VSV infection in the CNS. Groups of six mice were injected i.p. with either the control medium or 200 ng IL-12 on days 0–4 post infection. All mice were infected intranasally with VSV ($2 \times 10^5$ PFU/10 $\mu$L). On day four post infection, six mice from each group were sacrificed, and the mouse brains were homogenized for determination of viral titers on CHO cells. Viral titers of mice receiving IL-12 treatment were found to be significantly lower than those of the control mice, even in the NOS-3-KO mice, as determined by the Student's t test ($P<0.01$).
Figure 17:
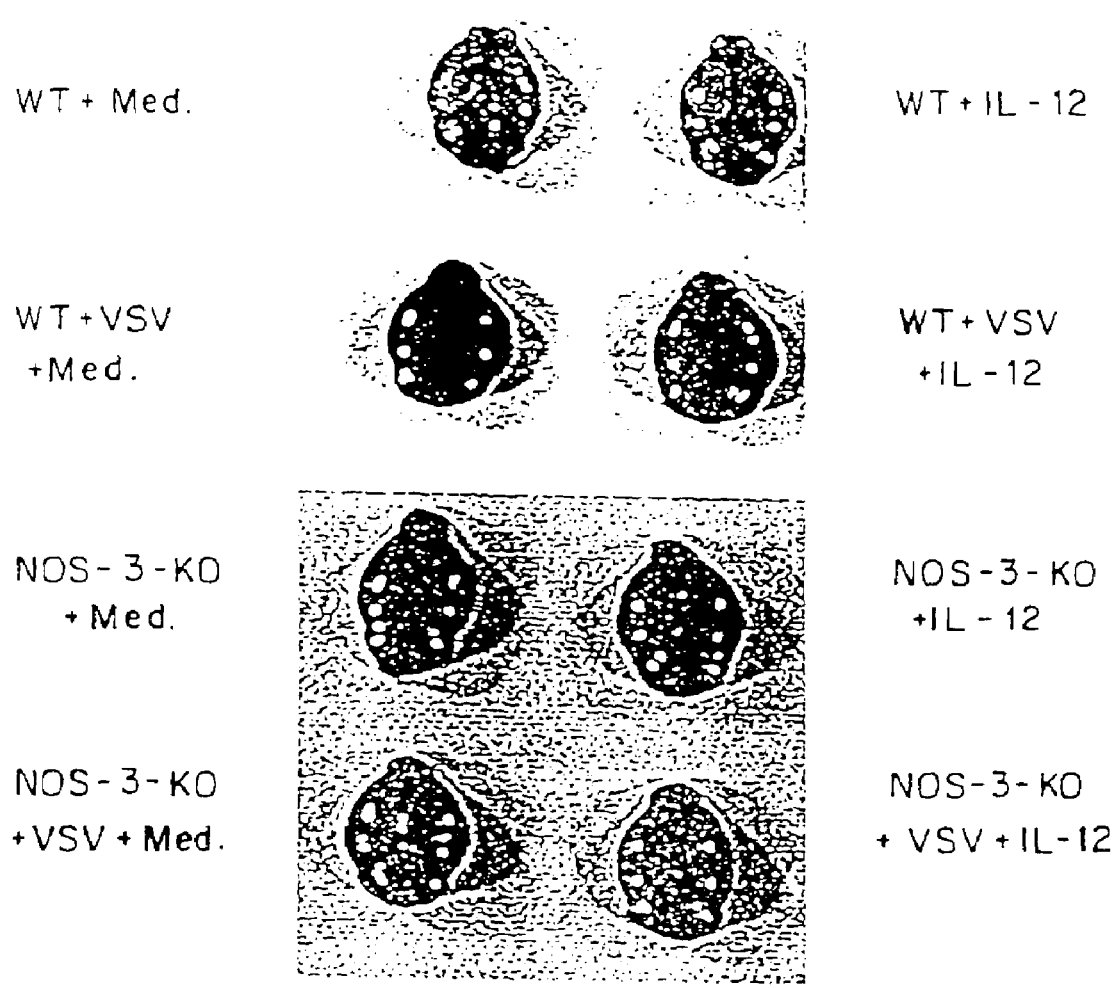
FIG. 17 shows the breakdown of the BBB following VSV infection. Three mice from each group were injected intravenously with 200 mL of 2% Evans blue at various time points. One hour later, the mice were sacrificed and perfused with normal saline. Brains were removed, and photos taken. One representative brain from each group is sown. VSV-infected WT mice showed breakage of the EBB by day eight post infection, but not the infected NOS-3 KO mice. IL-12-treated infected mice, as well as the uninfected control mice, did not show disruption of the BBB.
Figure 18:
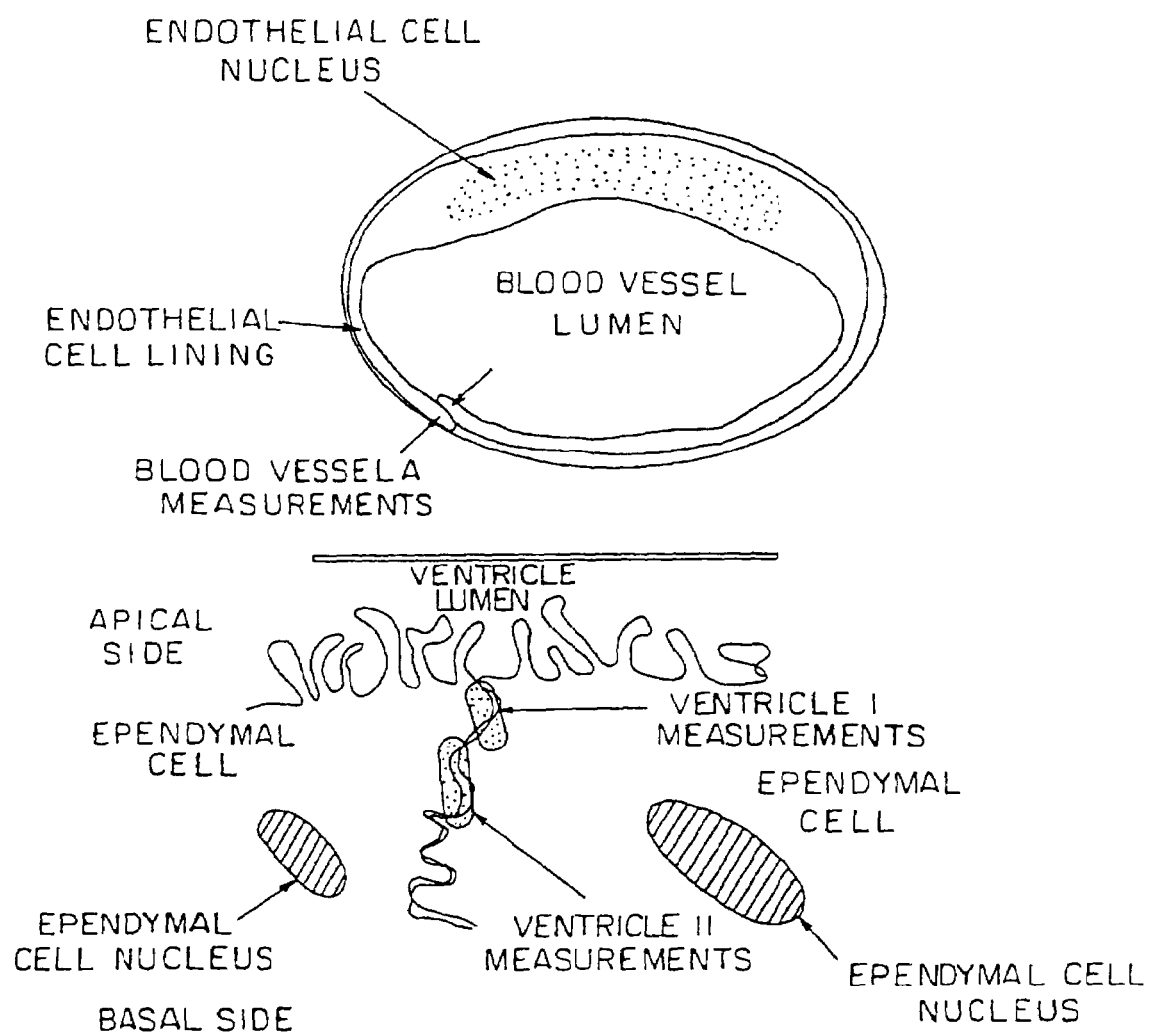
FIG. 18 is a diagrammatical depiction of areas from which data points were collected.
Figure 19A:
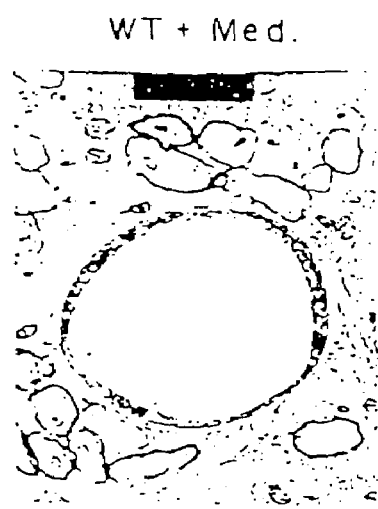
FIGS. 19A–19D show micrographs of the blood vessels of WT mice: WT+Med (FIG. 19A); WT+IL-12 (FIG. 19B); WT+VSV+Med (FIG. 19C); and WT+VSV+IL-12 (FIG. 19D). The mice were sacrificed at various time points, and the gap junctions were measured. Measurement areas are noted by an arrow.
Figure 19B:
Figure 19C:
Figure 19D:
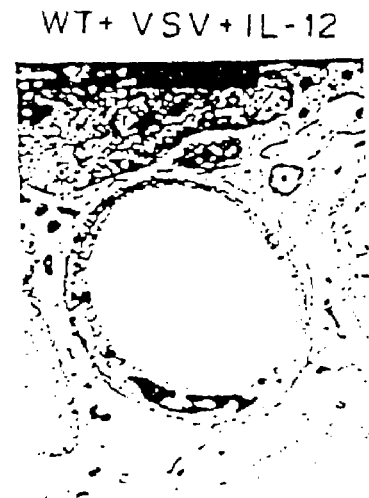
Figure 20A:
FIGS. 20A–20D show micrographs of the blood vessels of NOS-3 KO (N-3-KO) mice: N3-KO+Med (FIG. 20A); N3-KO+IL-12 (FIG. 20B); N3-KO+VSV+Med (FIG. 20C); and N-3KO+VSV+IL-12 (FIG. 20D). The mice were sacrificed at various time points, and the gap junctions were measured. Measurement areas are noted by an arrow.
Figure 20B:
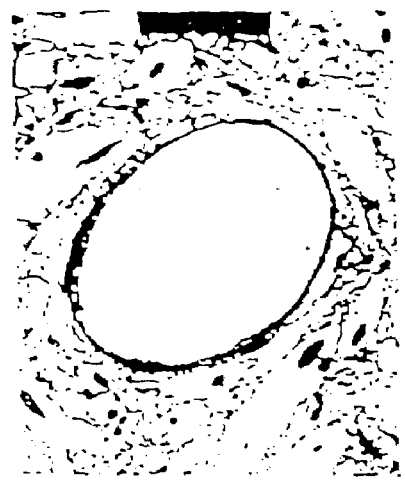
Figure 20C:
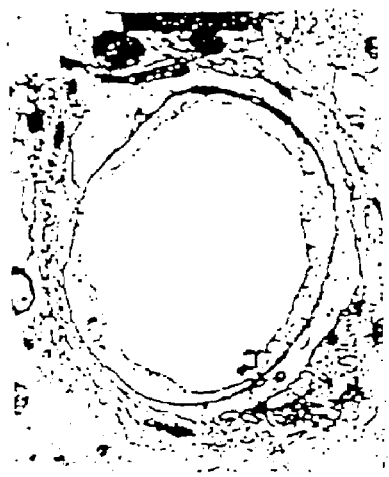
Figure 20D:
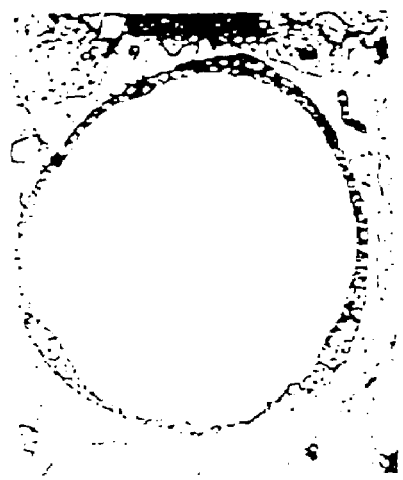
Figure 21A:
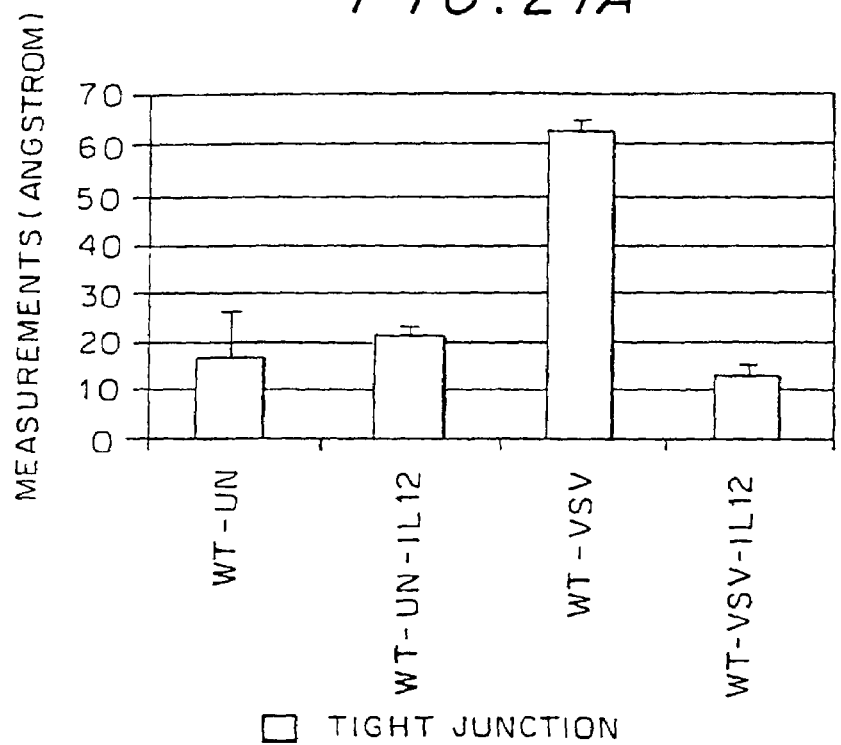
FIGS. 21A and 21B are graphical depictions of the average distance of the intercellular junction's gap between the endothelial cell lining of the blood vessel.
Figure 21B:
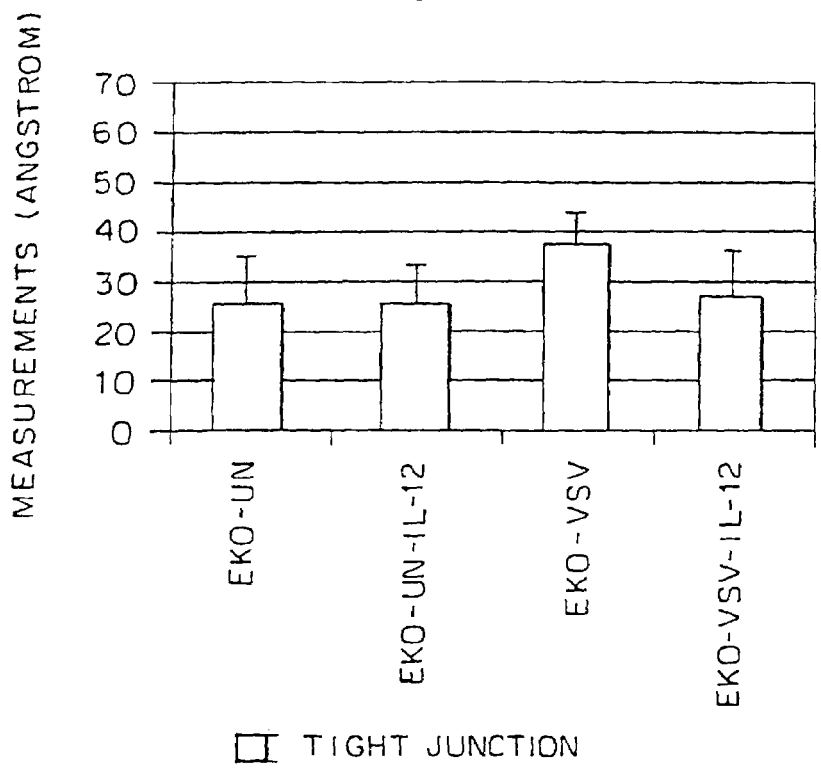
Figure 22A:
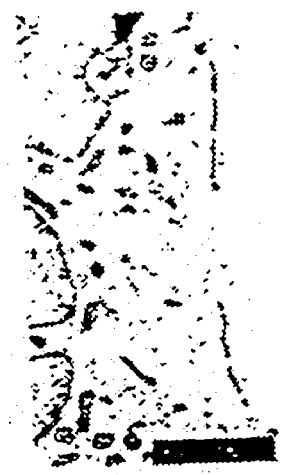
FIGS. 22A–22D are micrographs of the ependymal cells lining the fourth ventricle in WT mice: WT+Med (FIG. 22A); WT+IL-12 (FIG. 22B); WT+VSV+Med (FIG. 22C); and WT+VSV+IL-12 (FIG. 22D). The mice were sacrificed at various time points, and the gap junctions were measured.
Figure 22B:
Figure 22C:
Figure 22D:
Figure 23A:
FIGS. 23A–23D are micrographs of the ependymal cells lining the fourth ventricle in NOS-3 KO mice: N3-KO+Med (FIG. 23A); N3-KO+IL-12 (FIG. 23B); N3-KO+VSV+Med (FIG. 23C); and N3-KO+VSV+IL-12 (FIG. 23D). The mice were sacrificed at various time points, and the gap junctions were measured.
Figure 23B:
Figure 23C:
Figure 23D:
Figure 24A:
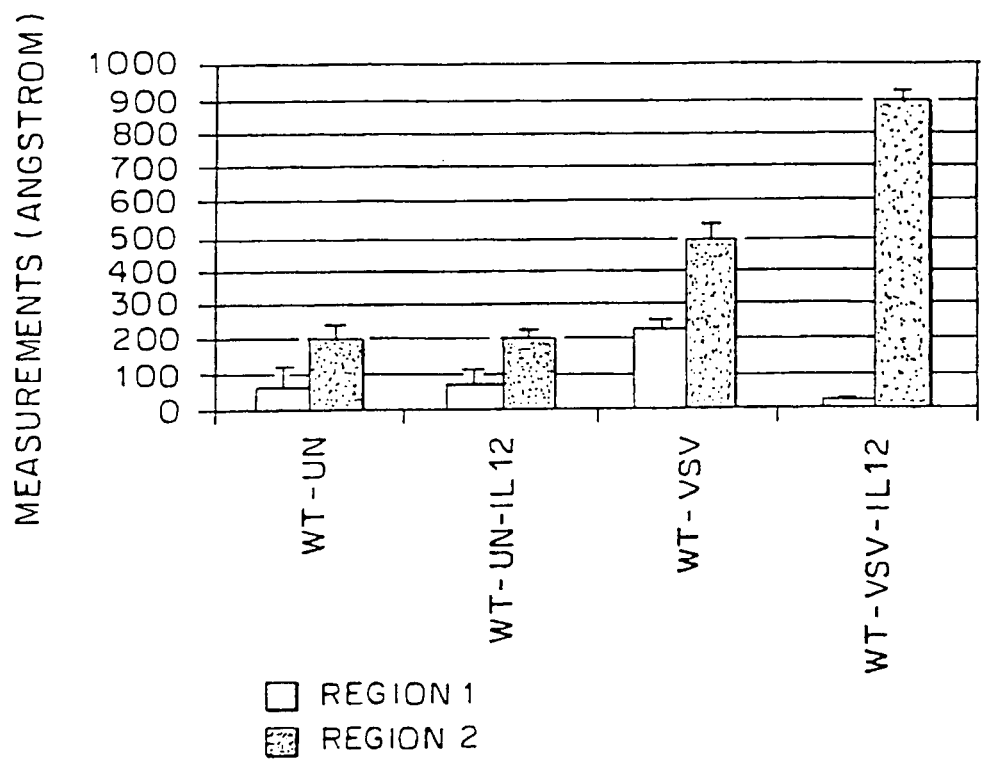
FIGS. 24A and 24B are graphical depictions of the average distance of the intercellular junction's gap between the ependymal cells which line the fourth ventricle of the CNS. All of the groups except WT+VSV showed no statistical difference in comparison to each other. All of these groups showed statistical difference from the WT+VSV group.
Figure 24B:
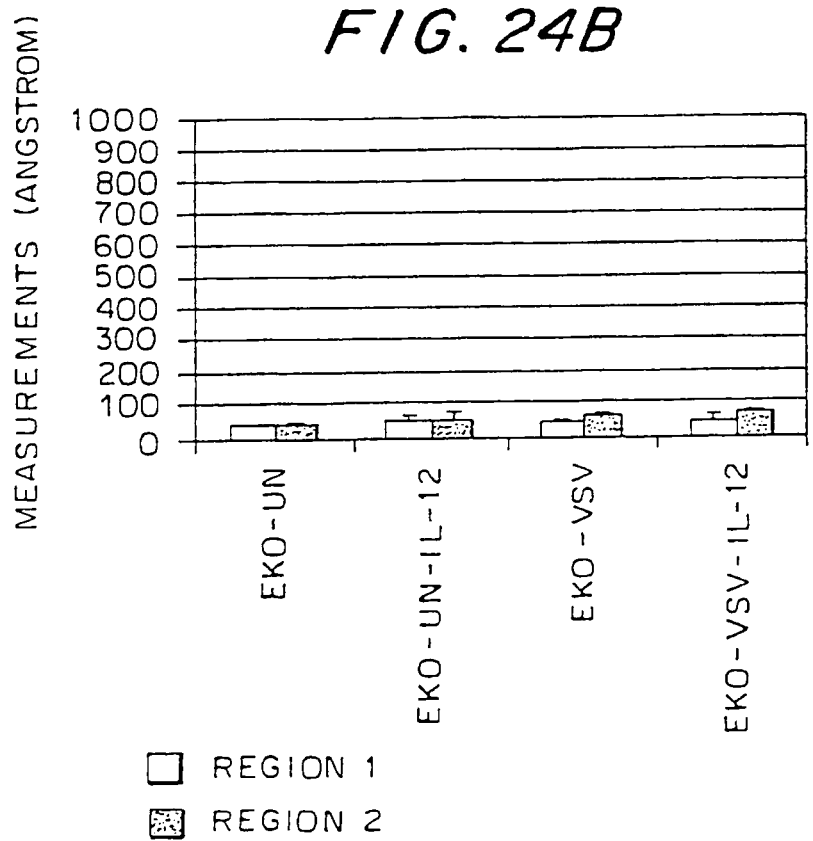

IL-12 Treatment Decreased VSV Titers in the Brain Homogenates, Even in the NOS-3 Knockout Mice The viral titers of mice treated with IL-12 were lower for both WT and NOS-3 KO mice than the control groups (FIG. 16). Injection of 200 ng of IL-12/mouse per day decreased the VSV titer about 100-fold for the WT mice and 100-fold for the NOS-3 KO mice. Immunohistochemical staining of VSV Ags on frozen sections from brains of other mice confirmed this observation.

IL-12 Treatment Enhanced the Expression of Both MHC Class I and Class II AGs

Neither infected B6 WT mice nor NOS-3 KO brain section expressed MHC Ags above the background level of immunchistochemical staining. However, four days following VSV infection, expression of MHC class I was observed in the OB of all groups (Tables 6A and 6B). Strongest staining of MHC class I coincided with VSV Ag+ areas. Induced expression of MHC class II was barely detected in the OB in the control groups, consistent with the earlier observations of the laboratory of the present inventors (Christian et al, 1996).

Following IL-12 treatment, expression of MHC Ags was significantly increased in both the wild-type and the knockout groups. MHC class I Ags was found in the OB, the hippocampal formation and along the fourth ventricle. Expression of MHC class II Ags was increased in many areas, particularly in the OB and the hippocampal formation (Tables 6A and 6B). In the absence of NOS-3, MHC was induced well above baseline levels, although it was lower than that of IL-12-treated WT mice.

IL-12 Treatment Induces Activation of Astrocytes and Microglia

The brain sections were stained for either glial fibrillary acidic protein (GFAP), a marker of astrocytes, or Mac-1 Ag expressed by microglial cells. IL-12 treatment resulted in more numerous and heavier-staining cells, suggesting astrocytosis and microgliosis (Tables 6A and 6B) The most pronounced astrocytosis and microgliosis was observed to coincide with VSV Ag+ areas.

TABLE 6A

IL-12 Treatment Induces CNS Parenchymal Changes in Both WT and NOS-3 KO Mice

| | Infected | | | | | | | | | | | |
|---|---|---|---|---|---|---|---|---|---|---|---|---|
| | WT | | | WT + IL-12 | | | NOS-3 KO | | | NOS-3 KO + IL-12 | | |
| Antigen | OB | HC | FV | OB | HC | FV | OB | HC | FV | OB | HC | FV |
| VSV | +++ | ++ | ++ | + | + | + | +++ | ++ | ++ | +++ | ++ | ++ |
| MHC-I | + | + | − | +++ | +++ | ++ | + | − | − | ++ | ++ | + |
| MHC-II | + | − | − | ++ | +++ | + | + | − | − | ++ | + | + |
| GFAP | 285 ± 9.5 | 96 ± 3.5 | 46.0 ± 5.7 | 395 ± 11.5 | 175 ± 21.5 | 76.0 ± 4.5 | 225 ± 15.0 | 65.0 ± 9.0 | 29.5 ± 31.0 | 365 ± 17.0 | 123 ± 13.0 | 60.0 ± 11.3 |
| Mac-1 | 30.0 ± 5.5 | 9.0 ± 1.5 | 10.0 ± 2.5 | 55.0 ± 5.0 | 28.0 ± 4.5 | 25.0 ± 3.5 | 19.0 ± 2.5 | 9.5 ± 4.1 | 6.0 ± 1.7 | 33.3 ± 3.1 | 21.5 ± 6.1 | 14.5 ± 5.1 |
| NOS-1 | 11.0 ± 3.6 | 22.0 ± 2.5 | 9.0 ± 2.0 | 32.0 ± 3.5 | 40.0 ± 2.5 | 20.0 ± 3.0 | 7.0 ± 2.5 | 12.0 ± 3.0 | 6.0 ± 5.5 | 23.5 ± 4.5 | 26.5 ± 3.1 | 16.0 ± 4.5 |
| NOS-2 | 48.0 ± 5.0 | 25.0 ± 2.0 | 25.0 ± 4.5 | 120 ± 10.0 | 65.0 ± 9.5 | 95.6 ± 4.5 | 42.3 ± 7.1 | 21.5 ± 4.5 | 21.3 ± 4.1 | 61.5 ± 6.5 | 46.5 ± 31.3 | 42.0 ± 5.0 |
| NOS-3 | 21.0 ± 2.5 | 15.0 ± 4.0 | 5.0 ± 1.7 | 59.0 ± 7.6 | 40.0 ± 2.0 | 20 ± 3.0 | 9.0 ± 2.0 | 6.5 ± 1.0 | 3.0 ± 0.4 | 11.0 ± 2.6 | 6.0 ± 2.0 | 5.6 ± 1.2 |
| NK1.1 | 26.0 ± 4.0 | 38.0 ± 6.5 | 30.0 ± 1.8 | 68.0 ± 4.1 | 68.0 ± 6.0 | 48.0 ± 6.4 | 11.5 ± 2.1 | 12.0 ± 7.4 | 22.0 ± 4.0 | 49 ± 6.6 | 55.0 ± 7.3 | 41 ± 5.7 |
| T cells | 26.5 ± 2.0 | 6.0 ± 2.0 | 1.0 ± 0.8 | 55.0 ± 8.1 | 22.0 ± 2.1 | 11.0 ± 1.5 | 36.0 ± 2.0 | 12.0 ± 3.4 | 4.0 ± 0.7 | 42.0 ± 6.1 | 24.0 ± 5.0 | 10.0 ± 3.1 |

TABLE 6B

IL-12 Treatment Induces CNS Parenchymal Changes in Both WT and NOS-3 KO Mice

| | Uninfected | | | | | | | | | | | |
|---|---|---|---|---|---|---|---|---|---|---|---|---|
| | WT | | | WT + IL-12 | | | NOS-3 KO | | | NOS-3 KO + IL-12 | | |
| | OB | HC | FV | OB | HC | FV | OB | HC | FV | OB | HC | FV |
| VSV | − | − | − | − | − | − | − | − | − | − | − | − |
| MHC-I | − | − | − | ++ | ++ | − | − | − | − | ++ | + | − |
| MHC-II | − | − | − | ++ | ++ | − | − | − | − | ++ | + | − |
| IFN-R | − | − | − | ++ | ++ | + | − | − | − | ++ | ++ | − |
| IL-12 | − | − | − | + | ++ | − | − | − | − | + | + | − |
| GFAP | 165 | 160 | 120 | 270 | 300 | 200 | 130 | 140 | 110 | 220 | 260 | 155 |
| Mac-1 | 10 | 7 | 6 | 18 | 10 | 15 | 10 | 6 | 7 | 21 | 6 | 6 |
| NOS-1 | 4 | 4 | 3 | 9 | 6 | 3 | 4 | 2 | 3 | 6 | 3 | 3 |

TABLE 6B-continued

IL-12 Treatment Induces CNS Parenchymal Changes in Both WT and NOS-3 KO Mice

| | Uninfected | | | | | | | | | | | |
|---|---|---|---|---|---|---|---|---|---|---|---|---|
| | WT | | | WT + IL-12 | | | NOS-3 KO | | | NOS-3 KO + IL-12 | | |
| | OB | HC | FV | OB | HC | FV | OB | HC | FV | OB | HC | FV |
| NOS-2 | 20 | 10 | 10 | 30 | 25 | 15 | 13 | 8 | 3 | 20 | 14 | 10 |
| NOS-3 | 12 | 10 | 5 | 20 | 12 | 12 | 6 | 5 | 5 | 7 | 3 | 5 |
| NK1.1 | 3 | 6 | 5 | 10 | 7 | 9 | 7 | 9 | 7 | 15 | 11 | 13 |
| T Cells | 3 | 1 | 1 | 0 | 4 | 3 | 1 | 2 | 2 | 3 | 5 | 3 |

Tables 6A and 6B: Sagittal sections of the three mouse brains of each group removed on day four post infection were stained with the respective antibodies. Positively stained cells (GFAP, Mac-1, NOS-1, NOS-2, NOS-3, NK1.1 and T cells) were counted under a light microscope. Relative intensity (VSV, MHC-I, MHC-II and IL-12) of staining in specific areas was examined and expressed at four different levels: − = no visual staining; + = minimal staining; ++ = moderate staining; +++ = strong staining (as previously characterized in Bi et al (1995b) and Christian (1996)). OB = olfactory bulb; HP = hippocampus. Underlined data has been shown to be statistically different, as described by Student's t test, $P < 0.05$.

IL-12 Treatment Induces NOS-1, NOS-2 and NOS-3 Expression

The laboratory of the present inventors has previously shown that nitric oxide has an inhibitory effect on VSV infection (Bi et al 1995a; Komatsu et al, 1996) and has observed that during infection, nitric oxide synthase (NOS) isoforms are induced and increased in immunohistochemical staining (Barna et al, 1996; Bi et al, 1995a; Bi et al 1995b; Christian et al, 1996; Komatsu et al, 1996). IFN—Y can activate NOS gene expression for all three isoforms (Barna et al, 1996; Kamijo et al, 1994; Komatsu et al, 1996). Therefore, the effects of IL-12 on NOS isoform expression during VSV infection were examined.

NOS-1 expression was poorly detected in neurons in the uninfected and control groups, as previously observed (Komatsu et al, 1996). Following IL-12 treatment, the expression was substantially increased in both the WT and NOS-3 KO mice (Tables 6A and 6B), although it was lower in NOS-3 KO mice.

NOS-2 expression by microglia and macrophages was found at low levels in the uninfected and control groups, consistent with the previous data from the laboratory of the present inventors (Bi et al, 1995a; Bi et al, 1995b). IL-12 treatment resulted in the higher NOS-2 expression in both WT and NOS-3 KO mice (Tables 6A and 6B); albeit lower in NOS-3 KO mice.

Expression of NOS-3 was previously observed in astrocytes and endothelial cells (Barna et al, 1996). IL-12 treatment induced the expression of NOS-3 in WT mice but was undetectable in NOS-3 KO mice (Tables 6A and 6B). Infiltration of VSV-Infected Brains by T Cells and NK Cells T cells were detected very infrequently in media-treated infected B6 and uninfected B6 mouse brains. IL-12 treatment resulted in the accumulations of CD4 and CD8 expressing T cells in the VSV-infected areas, such as the OB and HC (Tables 6A and 6B).

NK1.1 expressing cells were detected at relatively higher frequency in the infected media-treated than in uninfected brains (Tables 6A and 6B). A profound increase in the number of NK cells was found in the OB and other areas following IL-12 treatment in both WT and NOS-3 KO sections.

Breakdown of the BBB During VSV Infection

Some dyes, such as Evans blue, are normally excluded from the brain by intact BBB but can enter the brain when the integrity of the BBB is broken. This method is often used to assess simple alteration of the BBB (Bi et al, 1995; Doherty et al, 1974; Kandel et al, 1991). In WT VSV-infected medium-treated mice, the breakdown of the BBB was initially observed in the OB of the brain at day six post infection (Bi et al, 1995a). At day eight post infection, the BBB was obviously broken. IL-12-treated infected mice, as well as uninfected mice (medium or IL-12 treatment) did not show breakage of the BBB. In NOS-3 KO mice, the BBB was intact in all groups at both day eight post infection and day ten post infection, even in the infected medium-treated group. The sagittal sections of stained brains confirmed the penetration of the brain parenchyma by the dye.

Transmission Electron Microscope Analysis of VSV and IL-12 Treatment on the BBB

Eight groups of mice were tested:
Group A: WT+Medium
Group B: WT+IL-12
Group C: WT+Medium+VSV
Group D: WT+IL-12+VSV
Group E: NOS-3 KO+Medium
Group F: NOS-3 KO+IL-12
Group G: NOS-3 KO+Medium+VSV
Group H: NOS-3 KO+IL-12+VSV The mice were sacrificed at various time points (days 6 and 8 post infection for WT; days 8 and 10 post infection for NOS-3 KO). A graphical depiction of each group and the particular area of interest, whether it was the blood vessels or the ventricle ependymal cells, is represented in FIGS. 18, 19A–19D, 20A–20D and 22A–22D.

Discussion

IFN-γ was demonstrated in these studies to inhibit VSV replication through induction of the synthesis and activity of type I NOS in neurons in vitro (Tables 3 and 4) and in vivo (FIG. 3). This antiviral effect in culture was shown to be limited to VSV, but can be extended to HSV-1 (Table 3). Little is known about the mechanism(s) of IFN-γ regulation of type I NOS at present. It is possible that IFN-γ increases NOS gene expression at the transcription level, or IFN-γ increases quantity of NOS posttranscriptionally by either increasing the half-life of NOS mRNA or stabilizing the NOS protein. IFN regulatory factor (IRF)-1 is required in iNOS induction in mouse macrophage (Kamijo et al, 1994). IFN-γ signal transduction in neurons, however, may or may not be similar to that in other types of cells. Two closely linked, but separable, promoters of human type I NOS have been identified (Xie et al, 1995). The analysis of the sequence of the promoter region of human type I NOS suggested a STAT core element and possible sites for PIE and GAS. IRS, IRF-1, IFN-γ responsive sequence and interferon stimulation responsive elements were not found. However, the human type II NOS gene behaves differently than the mouse gene and is not readily inducible by IFN-γ, TNF-α or LPS (Reiling et al, 1994). There may be other cytokine response elements in the 5' region of the gene.

It has been previously demonstrated that IFN-γ can inhibit several viral infections in macrophages through iNOS induction (Karupiah et al, 1993). The results presented here are the first to report that IFN-γ can inhibit VSV in neurons through inducing type I NOS (Table 4). NO inhibits replication of HSV-1 in neurons (Table 3). Considering that NO-generating neurons are selectively resistant to neurotoxicity of NO (Dawson et al, 1994), one more advantage can be attributed to IFN-γ-mediated activation of OS in neurons in inhibiting viral infections in the CNS, rather than simply just induction of iNOS in neighboring neuroglial cells.

Alternative non-cytolytic means of clearing viral infections in neurons, such as antibody-mediated clearance have been demonstrated in other neurotropic viral infections (Levine et al, 1991; Dietschold et al, 1992). But since neither antibodies to VSV nor B cells infiltrating the CNS are observed before day ten, this mechanism is unlikely to be essential in clearance of VSV infection in the CNS in immunoincompetent mice (Bi et al, 1995b). Acute viral infection of neurons should be rapidly controlled by the host. While other anti-viral factors may exist, type I NOS may be the most important anti-viral factor of the host innate immunity existing in neurons.

Treatment of mice with IL-12 significantly inhibits VSV infection in the CNS in NOS-3 KO mice, but not in NOS-1 KO mice. IL-12 treatment was associated consistently and significantly decreased VSV titers in CNS (FIGS. 6 and 16), and VSV protein is detected in brain tissues (Tables 5A, 5B, 6A and 6B) of NOS-3 KO mice but not in NOS-1 KO mice. This was also observed in the survival and morbidity experiments as well (FIGS. 4, 5, 14 and 15). Interestingly, IL-12 had a positive effect on the immune response in both types of KO mice. This intervention was associated with induced expression of MHC class I and class II Ags, as well as the NOS isoforms not knocked out, albeit not to the levels in WT mice (Tables 5A, 5B, 6A and 6B). Astrocytosis and microgliosis was detected in the VSV Ag$^+$ areas (Tables 5A, 5B, 6A and 6B). In addition, IL-12 treatment resulted in the rapid infiltration of T cells and NK cells into the VSV-infected brains, although the levels in KO mice was not at the level of WT mice. The replication of VSV in NB41A3 cells was inhibited by the NO production of the cells (FIGS. 8 and 9). This anti-VSV effect may partially be due to the nitrosylation of the viral proteins (FIG. 10). Together, these results strongly suggest the involvement of activated NOS-1 in the anti-VSV mechanism in vitro and in vivo. Although the exact mechanism involved requires further study, this result was consistent with previous works (Harris et al, 1995; Komatsu et al, 1996; Lin et al, 1997).

VSV is a negative sense RNA virus which first transcribes its genome into mRNAs after uncoating and has to bear a complete set of viral enzymes in the virion to initiate a new round of the life cycle in infected cells. The results obtained by the present inventors from this study may implicate that NO may achieve its biological functions inside the cell by covalent and/or oxidative modifications of target molecules (Stamler et al, 1992; Stamler, 1994). There is accumulating evidence that NO has an inhibitory effect on a variety of virus infections (Reiss et al, 1998). It is frequently difficult to distinguish whether the inhibitory effect of NO is the consequence of the inhibition of cellular metabolism or of virus replication or both. For vaccinia virus, late stages of viral replication, which includes viral DNA replication and virion maturation, were inhibited by IFN-γ-induced NO (Harris et al, 1995). This may be due to the inhibition of ribonucleotide reductase (Kwon et al, 1991; Lepoivre et al, 1991), which is the rate-limiting enzyme in the DNA synthesis. Thus, by inactivating this enzyme, NO may be directly inhibiting viral DNA synthesis.

NO may be influencing several steps in the VSV life cycle to inhibit viral replication. It may be blocking viral RNA synthesis and decreasing viral protein accumulation. It may be nitrosylating the viral proteins, making them inactive. This anti-VSV effect of No is unlikely due to the direct cytotoxic effect of NO on infected cells (Lin et al, 1997). NO has been demonstrated to directly (Lancaster et al, 1990; Nathan, 1992; Pellat et al, 1990; Stamler et al, 1992) or indirectly (Drapier et al, 1986; Granger et al, 1980; Granger et al, 1982; Hibbs et al, 1990; Johnson et al, 1985) inhibit numerous cellular enzymes. Thus, NO may inactivate the viral enzymes required for viral RNA synthesis and may be blocking viral protein synthesis because the virus cannot sufficiently amplify viral mRNA.

NO had a single unpaired electron, making it a free radical. Most eukaryotic cells respond to stress, such as free radicals, by increasing the rate of intracellular proteolysis (Ciechanover et al, 1994). Thus, the IL-12-treated cells may be undergoing proteolysis, which increases the degradation of viral proteins accumulated in the cells. This may inhibit viral RNA synthesis by decreasing the amount of RNA-dependent RNA polymerase.

The neurons normally do not express MHC class I and II antigens. Thus, the utilization of NO as an antiviral component may be an essential strategy for activated neurons to retard viral dissemination from infected cells. The host may rely on NO to clear virus from the CNS during the early stages of infection without the cytolytic effects of NK and T cells (Bi et al, 1995a). It has been shown that in some cases NK cells can indirectly restrict viral replication without lysis of the virus-infected cells by stimulating NO production in macrophages (Karupiah et al, 1995). Thus, this type of inhibitory mechanism may furnish what is lacking in acquired immunity for virus clearance from the CNS (Lin et al, 1997).

The action of IL-12 and NO on the integrity of the BBB is reported here. In our model, IL-12 treatment alone was not enough to disrupt the integrity of the BBB (FIGS. 19A–19D, 20A–20D, 21A–21B, 22A–22D, 23A–23D and 24A–24B). However, infection with VSV resulted in disruption of the BBB in WT mice, consistent with previous work (Bi et al 1995b) (FIGS. 19A–19D, 20A–20D, 21A–21B, 22A–22D, 23A–23D and 24A–24B). In NOS-3 KO mice, infection did not result in BBB disruption. This shows the potential NO-induced disruption of the BBB.

NO has been implicated in the impairment of the integrity of the BBB in many types of clinical conditions (Boje, 1996; Buster et al, 1995; Chi et al, 1994; Hurst et al, 1996; Johnson et al, 1995; Thompson et al, 1992). In MS, a disease where one of the early crucial events is the perturbation of the BBB, elevated mRNA for NOS has been detected in post-mortem brain sections (Bo et al, 1994). Also, NADPH diaphorase activity has been observed in astrocytes from demyelinating lesions and the levels of nitrate and nitrite (stable end products of NO) are raised in the CSF.

Cytokines, such as TNF-α and various interleukins, have also been implicated in the BBB breakdown during bacterial sepsis (Goldblum et al, 1990; Tracey et al, 1990). Cytokines induce a disruption of the BBB at the level of the cerebral endothelial cells, in vitro (DeVries et al, 1995). These effects can be abolished in the presence of Indomethacin, a cyclooxygenase inhibitor (DeVries et al, 1996). In the present study, these inhibitors are shown to abolish the effects of the breakdown of the BBB in vivo, as well. This may be an indication that cytokines are activating the cerebral endothelial cells to produce eicosanoids, which subsequently induce the breakdown of the BBB. IL-1 and IL-6 have been shown to induce rat cerebral endothelial cells to produce large quantities of eicosanoids, mainly prostaglandin $E_2$ and thromboxane $A_2$ (Clark et al, 1988; DeVries et al, 1995), which may give rise to vasodilatory substances. $TxA_2$ receptor on endothelial cells has been associated with vasodilatory effects (Amin et al, 1997; Kent et al, 1993). Sodium salicylate can inhibit TNF-induced p42/p44 mitogen-activated protein kinase (Schewenger et al, 1996). Furthermore, the TNF-induced injury to aortic endothelial cells could be reduced in the presence of eicosanoid synthesis inhibitor BW 755c (Clark et al, 1988). Thus, cytokines released during inflammatory diseases of the CNS can exert a direct effect on the integrity of the BBB. The formation of eicosanoids by the cerebral endothelial cells are likely to play a key role in this process, which suggests a potential therapeutic effect of cyclooxygenase inhibitors on the BBB integrity during CNS inflammatory diseases.

A number of cytokines have been shown to enhance NOS activity (Durieu-Trautmann et al, 1993; Gross et al; 1991; Komatsu et al, 1996). Thus it is possible that cytokines may mediate BBB breakage through the generation of NO in the cells that constitute the BBB.

The mechanism(s) by which NO mediates the integrity of the EBB is still unknown. One possibility is that NO inhibits components of the mitochondrial respiratory chain and, hence, limit ATP synthesis (Brown, 1995). the regulation of ATP levels is considered important for the functioning of the BBB since the integrity of the tight junctions is energy dependent (Staddon et al, 1995). Increases in macromolecular permeability of endothelial monolayers have been observed under energy depletion (Plateel et al, 1995; Watanabe et al, 1991).

Having now fully described this invention, it will be appreciated that by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Akarid et al, *J. Virol.* 69:7001–7005 (1995)
Amin et al, *J. Inflamm.* 47:190–205 (1995a)
Amin et al, *Proc. Natl. Acad. Sci. USA* 92:7926–7930 (1995b)
Amin et al, *J. Clin. Invest.* 99:1231–1237 (1997)
Andersson et al, *J. Chem. Neuroanatomy* 6:7–18 (1993)
Anstey et al, *J. Exp. Med.* 184:557–567 (1996)
Ausubel et al, Eds., *Current Protocols In Molecular Biology*, Green Publishing Assoc., and Wiley Interscience (New York, 1987–1994)
Barna et al, *Virology* 223:331–343 (1996)
Beckman et al, *Am. J. Physiol.* 271:C1424–C1437 (1996)
Better et al, *Science* 240:1041–1043 (1988)
Bi et al, *J. Virol.* 69:2208–2213 (1995a)
Bi et al, *J. Virol.* 69:6466–6471 (1995b)
Bo et al, *Ann. Neurol.* 36:778–786 (1994)
Boje et al, *Eur. J. Pharmacol.* 272(2–3):297–300 (1995)
Boje, *Brain Res.* 720:75–83 (1996)
Bredt et al, *Proc. Natl. Acad. Sci. USA* 86:90300–90303 (1989)
Brightman et al, *J. Cell Biol.* 40:648–677 (1969)
Brown, *FEBS Lett.* 369:136–139 (1995)
Browning et al *J. Immunol.* 147:2685–2691 (1990)
Bundo-Morita et al, *Virol.* 163:622–624 (1988)
Buster et al, *Infect. Immun.* 63:3835–3839 (1995)
Butler et al, *Trends Pharmacol. Sci.* 16:18–22 (1995)
Cabilly et al, *Proc. Nat. Acad. Sci. USA* 81:3273–3277 (1984)
Cave et al, *J. Virol.* 50:86–96 (1984)
Chi et al, *Pharmacology* 48(6):367–373 (1994)
Chowdhury et al *Mol. Immunol.* 34:9–20 (1997)
Christian et al, *Viral Immunol.* 9:195–205 (1996)
Ciechanover et al, *FASEB J.* 8:182–191 (1994)
Clark et al, *Biochem.J.* 250:125–131 (1988)
Clewley et al, *J. Virol.* 23:152–166 (1977)
Coligan et al, Eds., *Current Protocols in Immunology*, Green Publishing Assoc., and Wiley Interscience (New York, 1993)
Cserr et al, *Immunol. Today* 13:507–512 (1992)

Dawson et al, *The Neuroscientist* preview issue:9 (1994)
DeGroot et al, *J. Neuropathol. Exp. Neurol.* 56:10–20 (1997)
DeVries et al, *J. Neuroimmunol.* 59:1–8 (1995)
DeVries et al, *J. Neuroimmunol.* 64:37–43 (1996)
Dietschold et al, *Proc. Nat. Acad. Sci.* 89:7252–7256 (1992)
Ding et al, *J. Immunol.* 141:2407–2413 (1988)
Dirnagle, *J. Cereb. Blood Flow Metab.* 16(6):1143–1152 (1996)
Doherty et al, *J. Immunol.* 112:1548–1552 (1974)
Drapier et al, *J. Cell. Physiol.* 78:790–797 (1986)
Durieu-Trautmann et al, *J. Cell. Physiol.* 155:104–111 (1993)
Fabry et al, *Immunol. Today* 15:218–224 (1994)
Farivar et al, *J. Biol. Chem.* 271:31585–31592 (1996)
Figini et al, *Cancer Res.* 58:991–996 (1998)
Forger et al, *J. Virol.* 65:4950–4958 (1991)
Fuller et al, *Cell* 38:65–77 (1984)
Furchgott et al, *Nature* 288:373–376 (1980)
Galea et al, *J. Neurosci. Res.* 37:406–414 (1994)
Gaston et al, *Am J. Respir. Crit. Care Med.* 149:538–551 (1994)
Goldblum et al, *Am. J. Physiol.* 258:L57–L67 (1990)
Granger et al, *J. CLin. Invest.* 65:357–37C (1980)
Granger et al, *J. Cell Biol.* 95:527–535 (1982)
Gross et al, *Biochem. Biophys. Res. Commun.* 178:823–829 (1991)
Harlow et al, *Antibodies: A Laboratory Manual*, Cold Spring Harbor Laboratory (1988)
Harris et al, *J. Virol.* 69:910–915 (1995)
Hibbs et al, in *Nitric Oxide from L-arginine: A Bioregulatory System*, Higgs, Ed., Elsevier Science Publishers, B.V. (Amsterdam, Netherlands, 1990)
Huang et al, *Nature* 226:325–327 (1970)
Huneycutt et al, *J. Virol.* 67–6698-6706 (1993)
Huneycutt et al, *Brain Res.* 635:81–95 (1994)
Hurst et al, *J. Cell. Physiol.* 167(1):89–94 (1996)
Iba et al, *Immunol. Cell Biol.* 75:217–221 (1997)
Janigro et al, *Circ. Res.* 75(3):528–538 (1994)
Johnson et al, *Neurol. Neurosurg. Psychiatr.* 58:107 (1995)
Johnson et al, *Ann. Neurol* 18:567–573 (1985)
Kakinuma et al, *Autoimmunity* 25:73–84 (1997)
Kamijo et al, *Science* 263:1612–1615 (1994)
Kandel et al, *Principles of Neurosicence* 3rd Ed., Elsevier Science Publishing Co. (NY, N.Y., 1991)
Karupiah et al, *Science* 261:1445–1448 (1993)
Karupiah et al, *J. Exp. Med.* 181:2171–2179 (1995)
Kent et al, *Circulation Res.* 72:958–965 (1993)
Kohler et al, *Nature* 256:495–497 (1975)
Komatsu et al *J. Neuroimmunology* 68:101–108 (1996)
Komatsu et al, *Viral Immun.* 10:35–47 (1997)
Kwon et al, *J. Exp. Med.* 174:761–767 (1991)
Lancaster et al, *Proc. Nat. Acad. Sci. USA* 87:1223–1227 (1990)
Lawson et al, *Proc. Nat. Acad. Sci. USA* 92:4477–4481 (1995)
Lee et al, *J. Exp. Med.* 180:365–369 (1994)
Leibowitz et al in *Immunology of the Immune System* (Arnold, Ed.), London (1983)
Lepoivre et al, *Biochem. Biophys. Res. Commun.* 179: 442–448 (1991)
Levine et al, *Science* 254:856–860 (1991)
Levy, *Cytokine Growth Factor Rev.* 8:81–90 (1997)
Lin et al, *J. Virol.* 71:5227–5235 (1997)
Liu et al, *Proc. Nat. Acad. Sci USA* 84:3439–3443 (1987)
Lotan et al, *FASEB J.* 8:1026–1033 (1994)
Lundh et al, *Neuropatho. and Applied Neurobio.* 13:111–122 (1987)
Lyles et al, *J. Virol.* 62:4387–4392 (1988)
Mannick et al in *Biology of Nitric Oxide, Part 5*, Samer et al, Eds., Portland Press (London, 1996)
Marietta, *Cell* 78:927–930 (1994)
Mayhan, *Brain Res.* 686:99–103 (1995)
Mayhan, *Brain Res.* 743(1–2):70–76 (1996)
Mayhan et al, *Stroke* 27(5):965–969 (1996)
Merill et al, *J. Immunol.* 151:2132–2141 (1993)
Mohammed et al, *Neuroscience* 35:355–363 (1990)
Moore et al, *Brit. J. Pharm.* 110:219–224 (1993)
Morrison et al, *Proc. Nat. Acad. Sci. USA* 81:6851–6855 (1984)
Moyer et al, *J. Virol.* 65:2170–2178 (1991)
Nakano et al, *Cancer* 56(17):4027–4031 (1996)
Nathan, *FASEB J.* 6:3051–3064 (1992)
Neuberger et al, *Nature* 314:268–270 (1985)
Nissim et al, *EMBO J.* 13:692 (1994)
Osbourn et al *Immunotechnology* 2:181–196 (1996)
O'Shea, *Immunity* 7:1–11 (1997)
Palmer et al, *Nature* 327:524–526 (1987)
Palmer et al, *Immunology* 91:473–478 (1997)
Pardridge, *Ann. N.Y. Acad. Sci.* 481:231–249 (1986)
Pellat et al, *Biochem. Biophys. Res. Commun.* 166:119–125 (1990)
Pereira et al, *J. Immunol. Methods* 203:11–24 (1997a)
Pereira et al, *Hybridoma* 16:11–16 (1997b)
Pfistermueller et al, *FEBS Lett.* 396:14–20 (1996)
Plakhov et al, *Virology* 209:257–262 (1995)
Plateel et al, *J. Neurochem.* 65:2138–2145 (1995)
Prado et al, *Stroke* 23:1118–1123 (1992)
Reichmann et al, *J. Virol.* 25:446–449 (1978)
Reiling et al, *Eur. J. Immunol.* 24:1941–1945 (1994)
Reiss, *Seminars in Virol.* 72:4547–4551 (1993)
Reiss et al, *J. Virol.* 72:4547–4551 (1998)
Sabin et al, *J. Exp. Med.* 66:15 (1937)
Sahagan et al, *J. Immunol.* 137:1066–1074 (1986)
Sawyer et al, *J. Immunol. Methods* 204:193–203 (1997)
Schewenger et al, *J. Biol. Chem.* 271:8089–8094 (1996)
Seguin et al, *J. Exp. Med.* 180:353–358 (1994)
Shiraishi et al, *J. Immunol.* 159:3549–3554 (1997)
Shukla et al, *NeuroReport* 6:1629–1632 (1995)
Shukla et al, *Experientia* 52(2):136–140 (1996)
Siegel et al, *J. Immunol. Methods* 206:73–85 (1997)
Staddon et al, *J. Cell. Sci.* 108:609–619 (1995)
Staeheli *Advances in Virus Research* 38:147–200 (1990)
Stamler et al, *Science* 258:1898–1902 (1992)
Stamler, *Cell* 78:931–936 (1994)
Stenger et al, *J. Exp. Med.* 180:783–793 (1994)
Stewart, *The Interferon System*, Springer Verlag, NY (1979)
Sun et al, *Proc. Nat. Acad. Sci. USA* 84:214–218 (1987)
Thompson et al, *Neurology* 24:60–63 (1992)
Tracey et al, *Adv. Surg.* 23:21–56 (1990)
Wagner in *The Rhabdovirus* (Wagner, Ed.) Plenum, New York (1987)
Wahl et al, *J. Nucl. Med.* 24:316–325 (1983)
Watanabe et al, *Am. J. Physiol.* 206:H1344–H1352 (1991)
Watters et al, *Immunotechnology* 3:21–29 (1997)
Winter et al, *Ann. Rev. Immunol.* 12:433–455 (1994)
Xie et al, *Proc. Nat. Acad. Sci. USA* 92:1242–1246 (1995)
Yun et al, *Crit. Rev. Neurobiol.* 10:291–316 (1996)
Zhang et al, *Stroke* 26:298–304 (1995)
Zhang et al, *J Nucl. Med.* 38(8):1273–1278 (1997)
Zielasek et al, *Cellular Immunology* 141:111–120 (1992)
Zinkernagel in *Fundamental Immunology* 3rd Ed. (Paul, Ed.) Raven Press (New York, 1993)

What is claimed is:

1. A method for increasing the permeability of the blood brain barrier, comprising administering to a subject a composition comprising a nitric oxide synthase-3 regulating agent which is a nitric oxide synthase-3 activator or a nitric oxide donor in a manner by which the nitric oxide synthase-3 regulating agent is delivered in an amount effective to transiently increase the permeability of the blood brain barrier, wherein the administering step administers to the subject a composition comprising a nitric oxide synthase-3 regulating agent associated with a targeting molecule specific for cells forming the blood brain barrier.

2. The method in accordance with claim 1, wherein the targeting molecule is a ligand or an antibody molecule.

3. The method in accordance with claim 1, wherein the cells to which the targeting molecule is specific are brain microvascular endothelial cells.

4. The method in accordance with claim 1, wherein the administering step is systemic administration to a subject.

5. The method in accordance with claim 1, wherein the nitric oxide synthase-3 regulating agent is in association with both a targeting molecule and a neurologically active therapeutic compound for delivery into the central nervous system following an increase in the permeability of the blood brain barrier.

6. The method in accordance with claim 1, wherein the nitric oxide synthase-3 regulating agent is in association with both a targeting molecule and a diagnostic compound for delivery into the central nervous system following an increase in the permeability of the blood brain barrier.

* * * * *

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
gaggatccag tggaataccc ggc				23

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
ccatccgagc cattcgacca catc				24

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
tcctattctc gtctagatca ggcg				24

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
gaccgagcag gatggcctct ttat				24

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
agaaattagg gatcgcacca cccc				24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
cgagaggctg gaattaggag agac				24

```
<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
tgcccaagag tcacaaggct attca                                 25

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
ccaaccttcg acaaagtcga ttgg                                  24

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
tgtaaactgc accacctctg gaac                                  24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
tatcgatggg tctagtaagt cggg                                  24
```